United States Patent [19]
Lee et al.

[11] Patent Number: 6,139,578
[45] Date of Patent: Oct. 31, 2000

[54] PREPARATION OF CELL SEEDED CERAMIC COMPOSITIONS

[75] Inventors: Dosuk D. Lee, Brookline, Mass.; Christian Rey, Castanet, France; Maria Aiolova, Brookline, Mass.

[73] Assignee: Etex Corporation, Cambridge, Mass.

[21] Appl. No.: 09/023,344

[22] Filed: Feb. 13, 1998

Related U.S. Application Data

[60] Division of application No. 08/729,354, Oct. 16, 1996, which is a continuation-in-part of application No. 08/650,764, May 20, 1996, which is a continuation-in-part of application No. 08/446,182, May 19, 1995, Pat. No. 5,676,976.

[51] Int. Cl.$^7$ .................................................. A61F 2/02
[52] U.S. Cl. ............................ 623/16.11; 623/23.61; 623/23.63
[58] Field of Search ........................... 623/23.61, 23.62, 623/23.63, 16.11; 424/423, 602, 440; 423/305, 308, 311

[56] References Cited

U.S. PATENT DOCUMENTS

| | | |
|---|---|---|
| Re. 33,161 | 2/1990 | Brown et al. . |
| Re. 33,221 | 5/1990 | Brown et al. . |
| 4,157,378 | 6/1979 | Tomlinson et al. . |
| 4,346,709 | 8/1982 | Schmitt . |

(List continued on next page.)

FOREIGN PATENT DOCUMENTS

| | | |
|---|---|---|
| 0347028 | 11/1989 | European Pat. Off. . |
| 0664133 | 7/1995 | European Pat. Off. . |
| 0 268 463 | 2/1998 | European Pat. Off. . |
| 63-111 875 | 5/1988 | Japan . |
| 63-170205 | 7/1988 | Japan . |
| 2-182261 | 7/1990 | Japan . |
| 5-305134 | 11/1993 | Japan . |
| 6-228 011 | 8/1994 | Japan . |
| 7-277 712 | 10/1995 | Japan . |
| WO 92/02453 | 7/1991 | WIPO . |
| WO 92 00109 | 9/1992 | WIPO . |
| WO 94/04657 | 8/1993 | WIPO . |
| WO 94/02412 | 2/1994 | WIPO . |
| WO 94 20064 | 9/1994 | WIPO . |
| WO 95/08319 | 9/1994 | WIPO . |
| WO 94/25080 | 11/1994 | WIPO . |
| WO 96/03160 | 2/1996 | WIPO . |
| WO 96/36562 | 5/1996 | WIPO . |
| WO 97/17285 | 11/1996 | WIPO . |

OTHER PUBLICATIONS

Aoki, "Science and medical applications of hydroxyapatite", *JAAS*, 11–15, 1991.

Appel et al., "Recent advances in implants for bone growth promotion", *Exp. Opin. Ther. Patents*, 4:1461, 1994.

Atala et al., "Injectable alginate seeded with chondrocytes as a potential treatment for vesicoureteral reflux", *J. Urol.*, 150:745, 1993.

Athanasou et al., "Current Concepts Review: Cellular Biology of Bone–Resorbing Cells", *J. Bone and Joint Surg.*, 78–A:1096–1112, 1996.

Attawia et al., "Osteoblast–like cell adherence and migration through 3–dimensional porous polymer matrices", *Bioch. Biophyr. Res. Commun.*, 213:639, 1995.

(List continued on next page.)

*Primary Examiner*—David J. Isabella
*Attorney, Agent, or Firm*—Clark & Elbing LLP; Mary Rose Scozzafava

[57] ABSTRACT

The present invention provides a synthetic, poorly-crystalline apatitic (PCA) calcium phosphate material seeded with cells. Preferably, the cells are tissue-forming or tissue-degrading cells. The compositions provided by the present invention are useful for a variety of applications, including in vivo and in vitro tissue growth (preferably bone or cartilage), osseous augmentation, and methods of diagnosing disease states by assaying tissue-forming potential of cells isolated from a host. The invention also provides in vitro cell culture systems and cell encapsulation matrices.

30 Claims, 17 Drawing Sheets

U.S. PATENT DOCUMENTS

| | | |
|---|---|---|
| 4,347,234 | 8/1982 | Wahlig et al. . |
| 4,353,888 | 10/1982 | Sefton . |
| 4,429,691 | 2/1984 | Niwa et al. . |
| 4,609,551 | 9/1986 | Caplan et al. . |
| 4,612,053 | 9/1986 | Brown et al. . |
| 4,620,327 | 11/1986 | Caplan et al. . |
| 4,684,673 | 8/1987 | Adachi . |
| 4,737,411 | 4/1988 | Graves, Jr. et al. . |
| 4,842,603 | 6/1989 | Draenert . |
| 4,849,193 | 7/1989 | Palmer et al. . |
| 4,880,610 | 11/1989 | Constantz . |
| 4,892,538 | 1/1990 | Aebischer et al. . |
| 4,917,702 | 4/1990 | Scheicher et al. . |
| 4,938,938 | 7/1990 | Ewers et al. . |
| 4,959,104 | 9/1990 | Iino et al. . |
| 5,007,930 | 4/1991 | Dorman et al. . |
| 5,034,059 | 7/1991 | Constantz . |
| 5,037,639 | 8/1991 | Tung . |
| 5,041,138 | 8/1991 | Vacanti et al. . |
| 5,047,031 | 9/1991 | Constantz . |
| 5,053,212 | 10/1991 | Constantz et al. . |
| 5,085,861 | 2/1992 | Gerhart et al. . |
| 5,129,905 | 7/1992 | Constantz . |
| 5,149,368 | 9/1992 | Liu et al. . |
| 5,152,836 | 10/1992 | Hirano et al. . |
| 5,164,187 | 11/1992 | Constantz et al. . |
| 5,178,845 | 1/1993 | Constantz et al. . |
| 5,197,985 | 3/1993 | Caplan et al. . |
| 5,226,914 | 7/1993 | Caplan et al. . |
| 5,262,166 | 11/1993 | Liu et al. . |
| 5,279,831 | 1/1994 | Constantz et al. . |
| 5,281,265 | 1/1994 | Liu . |
| 5,286,763 | 2/1994 | Gerhart et al. . |
| 5,336,264 | 8/1994 | Constantz et al. . |
| 5,342,441 | 8/1994 | Mandai et al. . |
| 5,352,715 | 10/1994 | Wallace et al. . |
| 5,399,665 | 3/1995 | Barrera et al. . |
| 5,470,803 | 11/1995 | Bonfield et al. . |
| 5,486,359 | 1/1996 | Caplan et al. . |
| 5,496,399 | 3/1996 | Ison et al. . |
| 5,514,378 | 5/1996 | Mikos et al. . |
| 5,516,532 | 5/1996 | Atala et al. . |
| 5,522,893 | 6/1996 | Chow et al. . |
| 5,525,148 | 6/1996 | Chow et al. . |
| 5,542,973 | 8/1996 | Chow et al. . |
| 5,545,254 | 8/1996 | Chow et al. . |
| 5,565,502 | 10/1996 | Glimcher et al. . |
| 5,691,397 | 11/1997 | Glimcher et al. . |
| 5,700,289 | 12/1997 | Breitbart et al. ............... 623/16 |

OTHER PUBLICATIONS

Attawia et al., "Immunofluorescence and confocal laser scanning microscopy studies of osteoblast growth and phenotypic expression in three–dimensional degradable synthetic matrices", *J. Biomed. Mater. Res.*, 29:843, 1995.

Attawia et al., "The long term osteoblast response to poly (anhydride–co–imides): A new degradable polymer for use in bone," *Fifth World Cong.*, May 29–Jun. 2, 1996, Toronto, Canada.

Barton et al "Surface and bulk properties of amorphous calcium phosphate" *Colloid Interface Sci.* [Proc. Int. Conf.], 50th 3:71 (1976) [CA 87:73954v].

Besic et al., "Electron probe microanalysis of noncarious enamel and dentin and calcified tissues in mottled teeth", *J. Dent. Res.*, 48:131, (Jan.–Feb, 1969).

Blumenthal et al. "Effect of Preparation Conditions on the Properties and Transformation of Amorphous Calcium Phosphate", *Mat Res. Bull.*, 7(11):1181 (Nov. 1972).

Boskey, Adele, "Matrix Proteins and Mineralization: An Overview", *Connect. Tissue Res.*, 35:(1–4):357–63, 1996.

Chu et al., "Articular cartilage repair using allogeneic perichondrocyte–seeded biodegradable porous polylactic acid (PLA): a tissue–engineering study", J. Biomed. Mater. Res., 29:1147, 1995.

Constantz et al., "Skeletal repair by in situ formation of the mineral phase of bone", *Sci..* 267:1976, 1995.

Driessens et al., "Calcium Phosphate Bone Cements" *Encycl. Hndbk. of Biomat. and Bioeng.*, Wise (EDS) NY, Marcel Dekker, 1995.

Ducheyne et al., "Bioceramic Composites", Chapter 15 from "An Introduction to Bioceramics, Advanced Series in Ceramics", vol. I.

Eanes et al., "Intermediate states in the precipitation of hydroxyapatite", *Nature*, 208:365–367, Oct. 23, 1965.

Eanes et al. "Intermediate phases in the basic solution preparation of alkaline earth phosphates" *Calcif. Tiss. Res.*, 2(1):38 (1968) [CA 69:110373f].

Eanes, "Thermochemical studies on amorphous calcium phosphate", *Calc. Tiss. Res.*, 5:133, 1970.

Elgendy et al., "Osteoblast–like cell (MC3T3–E1) proliferation on bioerodible polymers: an approach towards the development of a bone–bioerodible polymer composite material", *Biomater.*, 14:263, 1993.

Etex (Goad et al) "Resorbable Apatitic Bone Substitute Material" 1997 *ASBMR Abstract*; 12 (1):s518, Aug., 1997.

Etex (Knaack et al) "Novel Fully Resorbable Calcium Phosphate Bone Substitute" 1997 *ASBMR Abstract*, vol. 12, Supplement 1:s202 Aug., 1997.

Etex (Knaack et al) "A Fully Resorbable Calcium Phosphate Bone Substitute" *Portland Bone Symp.*, 1997.

Etex (D. Knaack) "Endothermically Setting Caclium Phosphate Bone Substitute" *Orthop. Cong.*, Aug. 20–22, 1997, Boston MA.

Fabbri et al., "Hydroxyapatite–based porous aggregates: physico–chemical nature, structure, texture and architecture", *Biomat.*, 16:225–228, 1995.

Freed et al., "Cultivation of cell–polymer cartilage implants in bioractors", *J. Cell. Biochem.*, 51:257, Mar. 1993.

Freed et al., "Biodegradable polymer scaffolds for tissue engineering", *Bio/Tech.*, 12:689, 1994.

Gao, T.J., "Established competence of bioactive composite bone substitute on the healing of diaphyseal segmental defects in sheep," *Fifth World Cong.*, May 29–Jun. 2, 1996, Toronto, Canada.

Glimcher et al., "Recent studies of bone mineral: Is the amorphous calcium phosphate theory valid?", *J. of Cryst. Growth*, 53:100–119, 1981.

Glimcher, "Recent studies of the mineral phase in bone and its possible linkage to the organic matrix by protein–bound phosphate bonds", *Phil. Trans. R. Soc. Lond.*, B 304:479–508, 1984.

Graves et al., "Resorbable ceramic implants", *J. Biomed. Mater. Res. Symp.*, No. 2 (part 1), 9–115, 1971.

Greenfield et al., "Formation chemistry of amorphous calcium phosphates prepared from carbonate containing solutions", *Calc. Tiss. Res.*, 9:152, 1972.

Hirasawa et al., "Manufacture of high purity hydroxyapatite", Chem. Abstr., 108 (10):166, No. 78193h (Mar. 7, 1988).

Holmes et al., "Surface areas by gas adsorption on amorphous calcium phosphate and crystalline hydroxyapatite", *Calc. Tiss. Res.*, 7:163, 1971.

Hubbell, "Biomaterials in tissue engineering", *Bio/Tech.*, 13:56, 1995.

Ishaug et al., "Osteoblast function on synthetic biodegradable polymers", *J. Biomed. Mater.Res.*, 28:1445, Dec. 1994.

Ishikawa et al., "Effects of preparation in aqueous solution on properties of hydroxyapatites" *Dent. Mater. J.*, 9(1):58 (1990) [CA 113:218168j].

Jang, B.Z., "Advanced Polymer Composites", Ch.1, Intro., *The Mater. Info. Soc.*

Kim et al., "Hyaluronan–based biodegradable scaffolds for skeletal tissue reconstruction," *Fifth World Biomat. Cong.*, May 29–Jun. 2, 1996, Toronto, Canada.

Labarthe et al., "Sur la structure et les propriétés des apatites carbonatées de type B phospho–calciques", *Ann. Chem.*, 8:289, 1973.

Morro et al., "Surface modification of three–dimensional matrices for tissue–engineering", *Fifth World Biomat. Cong.*, May 29–Jun. 2, 1996, Toronto, Canada.

Nolan et al., "Calcium hydroxyapatite ceramic delivery system", *J. Bone and Joint Surg.*, 75–13:334, 1993.

Nylen et al., "Molecular and ultrastructural studies of non–crystalline calcium phosphates", *Calc. Tiss. Res.*, 9:95, 1972.

Otsuka et al., "Effect of particle size of metastable calcium phosphates on mechanical strength of a novel self–setting bioactive calcium phosphate cement", *J. of Biomed. Mater. Res.*, 29:25–32, 1995.

Otsuka et al., "A novel skeletal drug delivery system using self–setting calcium phosphate cement. 9:Effects of the mixing solution volume on anticancer drug release from homogeneous drug–loaded cement", *J. of Pharm. Sci.*, 84(6), Jun. 1995.

Otsuka et al., "A novel skeletal drug–delivery system using self–setting calcium phosphate cement. 4. Effects of the mixing solution volume on the drug–release rate of heterogeneous aspirin–loaded cement", *J. of Pharm. Sci.*, 83(2), Feb. 1994.

Pool, "Coral chemistry leads to human bone repair", *Sci.*, 269:1772 (Mar., 1995).

Posner et al., "Synthetic amorphous calcium phosphate and its relation to bone mineral structure", Bone Min. Struc., 8:273–281, 1975.

Rey et al., "The carbonate environment in bone mineral: a resolution–enhanced fourier transform infrared spectroscopy study", *Calcif. Tiss. Int.*, 45:157, 1989.

Rey et al., "Structural studies of the mineral phase of calcifying cartilage"*J. Bone Min. Res.*, 6:515, 1991.

Rey et al., "Preparation of Microporous Ceramic at Low Temperature from Poorly Crystalline Apatite" *Symposium Abstract*, 1993.

Roodman, G. David, "Advances in Bone Biology: The Osteoclast", *Endo. Rev.*, 17(4):308–332, 1996.

Suzuki et al., "Identification Macrophage Migration Inhibitoty Gactor in Murine Neonatal Clavariae and Osteoblasts", *43rd Ann. Mtng, Orthop. Res. Soc.*, Feb. 9–13, 1997, San Francisco, CA.

Thomson et al., "Fabrication of biogradable polymer scaffolds to engineer trabecular bone", *J. Biomater. Sci. Polymer Edn.*, 7:23, 1995.

Tona et al., "Derivatized hyaluronic acid films support mesenchymal stem cell attachment and proliferation", *Fifth World Biomat. Cong.*, May 29–Jun. 2, 1996, Toronto, Canada.

Törmälä, "Biodegradable self–reinforced composite materials; manufacturing structure and mechanical properties", *Clin. Mat.*, 10:29, 1992.

Tung et al., "In vitro drug release of antibiotic–loaded porous hydroxyapatite cement", *Art. Cell, Blood Subs., and Immob. Biotech.*, 23(1), p. 81–88, 1995.

Van Valkenburg, J., "Biological bone graft substitute helps body heal itself", *Commerical Appeal*, B4 (Aug. 22, 1996).

Rey et al., "Chemical Properties of Poorly Crystalline Apatites" *Phosphorus Res. Bull.* 6:67–70 (1996) (Abstracts only).

PREPARATION OF CELL SEEDED CERAMIC COMPOSITIONS

This application is a divisional of co-pending application U.S. Ser. No. 08/729,354 filed Oct. 16, 1996 entitled "Cell Seeding of Ceramic Compositions", which is a continuation-in-part application of co-pending application U.S. Ser. No. 08/650,764 filed May 20, 1996 entitled "Novel Bone Substitution Material and a Method of Its Manufacture", which is a continuation-in-part application of application U.S. Ser. No. 08/446,182 filed May 19, 1995, now U.S. Pat. No. 5,676,976 entitled "Synthesis of Reactive Amorphous Calcium Phosphates", each of which is incorporated herein by reference. This application is also related to commonly-owned applications U.S. Ser. No. 08/729,342 entitled "Delivery Vehicle", U.S. Ser. No. 08/729,344 entitled "Method and Products Related to the Physical Conversion of Reactive Amorphous Calcium Phosphate", U.S. Ser. No. 08/729,343 entitled "Orthopedic and Dental Ceramic Implants", and U.S. Ser. No. 07/732,016 entitled "Bioactive Ceramic Composites", each of which was filed on Oct. 16, 1996 and is incorporated herein by reference.

BACKGROUND OF THE INVENTION

One of the goals of reconstructive surgery is to be able to replace damaged tissue with new tissue, perhaps grown from a patient's own cells. For example, researchers have endeavored to develop cartilage regeneration systems in which isolated chondrocytes are injected into a damaged area in the context of a polymer scaffold (see, for example, Atala et al., *J. Urol.* 150:747, 1993; Freed et al., *J. Cell. Biochem.* 51:257, 1993 and references cited therein). Similar seeded scaffold systems have been studied in the context of bone repair, where osteoblast cells are utilized in conjunction with polymeric or ceramic supports (see, for example, Elgendy et al., *Biomater.* 14:263, 1993; Ishaug et al., *J. Biomed. Mater. Res.* 28:1445, 1994). Seeded compositions have also been studied for their utility in bladder control and vesicoureteral applications (see, for example, Griffith-Cima et al., published PCT application no. WO 94/25080.

Researchers in the field have identified several characteristics that are desirable for scaffold materials to be used in such seeded compositions. For example, Freed et al. (*Bio/Technology* 12:689, 1994) list the following six factors as desirable features:

(1) the scaffold surface should permit cell adhesion and growth;

(2) neither the scaffold material nor its degradation products should provoke inflammation or toxicity when implanted in vivo;

(3) the scaffold material should be reproducibly processable into three dimensional structures;

(4) the scaffold material should have a porosity of at least 90% so that it provides high surface area for cell-scaffold interactions, sufficient space for extracellular matrix regeneration, and minimal diffusion constraints during in vitro culture;

(5) the scaffold material should resorb once it has served its purpose of providing a template for the regenerating tissue; and (6) the scaffold degradation rate should be adjustable to match the rate of tissue regeneration by the cell type of interest.

Much effort has been spent in attempts to identify materials that can act as effective scaffolds for tissue repair. There remains a need for the development of suitable new materials for use as scaffolds in cell seeding applications.

Definitions

"Amorphous"—By "amorphous" as that term is used here, it is meant a material with significant amorphous character. Significant amorphous character contemplates greater than 75% amorphous content, preferably greater than 90% amorphous content, and is characterized by a broad, featureless X-ray diffraction pattern. It is recognized that a small degree of crystallinity may exist in the material. However, for the amorphous precursor materials of the present invention, it is preferable that the degree of crystallinity be less than that desired in the product material.

"Bioactive"—"Bioactive" refers to a material that induces hard tissue formation in and about the implant. When implanted in soft tissue, the bioactivity may also require the presence of a growth or trophic factor, or the seeding of the implant with a hard tissue forming cell type.

"Biocompatible"—The term "biocompatible", as used herein, means that the material does not elicit a substantial detrimental response in the host. There is always concern, when a foreign object is introduced into a living body, that the object will induce an immune reaction, such as an inflammatory response that will have negative effects on the host. For example, although hydroxyapatite is generally considered to be "biocompatible", significant inflammation and tissue necrosis have been observed when crystalline hydroxyapatite microcarriers are inserted intramuscularly in animals (see, for example, IJntema et al., *Int. J. Pharm* 112:215, 1994).

"Bioresorbable"—"Bioresorbable" refers to the ability of a material to be resorbed in vivo. "Full" resorption means that no significant extracellular fragments remain. The resorption process involves elimination of the original implant materials through the action of body fluids, enzymes or cells. Resorbed calcium phosphate may, for example, be redeposited as bone mineral, or by being otherwise reutilized within the body, or excreted. "Strongly bioresorbable", as that term is used herein, means that at least 80% of the total mass of material implanted intramuscularly or subcutaneously is resorbed within one year. In preferred embodiments of the invention, the strongly resorbing PCA calcium phosphate is characterized in that, when at least 1 g (preferably 1–5 g) of PCA material is implanted at a subcutaneous or intramuscular site, at least 80% of the material is resorbed w/in one year. In more preferred embodiments, the material will be resorbed within nine months, six months, three months, and ideally one month. Furthermore, particularly preferred materials are characterized in that they can be fully resorbed in the stated time periods. For the purpose of this disclosure, "weakly" resorbable means that less than 80% of the starting material is resorbed after one year.

"Cells"—the term "cells", as used herein, refers to any preparation of living tissue, including primary tissue explants and preparations thereof, isolated cells, cells lines (including transformed cells), and host cells.

"Effective Amount"—An effective amount of a biologically active agent is an amount sufficient to elicit a desired biological response.

"Hardening"—"Hardening" refers to the process by which the hydrated precursor is transformed into a hardened PCA material. The PCA material is considered to be "hardened" when it is a substantially non-formable solid. Such a hardened PCA material has minimal compressibility and tends to undergo plastic as opposed to elastic deformation.

"Hydrated precursor"—The term "hydrated precursor", as used herein, refers to the paste or putty formed by hydration of the dry PCA precursors in the presence of a limited amount of aqueous solution (i.e., less than approximately 1 mL aqueous solution/1 g precursor powder). The hydrated precursor may comprise both reactants and products, in various combinations, depending on the extent to which the conversion has progressed. Both the "injectable" and "formable" PCA precursor pastes described herein are hydrated precursors. Preferred "injectable" hydrated precursors have a consistency appropriate for delivery through an 18 gauge needle.

"Poorly crystalline apatitic calcium phosphate", "PCA calcium phosphate" and "PCA material", as those terms are used herein, describe a synthetic poorly crystalline apatitic calcium phosphate. The PCA material is not necessarily restricted to a single calcium phosphate phase provided it has the characteristic XRD and FTIR pattern. A PCA calcium phosphate has substantially the same X-ray diffraction spectrum as bone. The spectrum is generally characterized by only two broad peaks in the region of 20–35° with one centered at 26° and the other centered at 32°. It is further characterized by FTIR peaks at 563 $cm^{-1}$, 1034 $cm^{-1}$, 1638 $cm^{-1}$ and 3432 $cm^{-1}$ (±2 $cm^{-1}$). Sharp shoulders are observed at 603 $cm^{-1}$ and 875 $cm^{-1}$, with a doublet having maxima at 1422 $cm^{-1}$ and 1457 $cm^{-1}$.

"Promoter"—The term "promoter", as used herein, describes a material or treatment that promotes hardening of a hydrated precursor and may enhance the ACP to PCA calcium phosphate conversion. Some promoters participate in the conversion and are incorporated into the product PCA material; others, known as "passive" promoters, do not participate.

"Reactive"—"Reactive" is used herein to refer to the ability of an amorphous calcium phosphate when mixed with liquid to form a hydrated precursor to undergo conversion to the PCA material of the present invention in the presence of a promoter in association with hardening of the precursor materials. Preferred ACPs are characterized by an ability to convert completely, an ability to convert quickly with hardening, an ability to undergo conversion with otherwise inert compounds and/or an ability to convert into a substantially homogeneous PCA material. Where the ACP is reacted with a second calcium phosphate, the "conversion" can encompass conversion of both the ACP and the second calcium phosphate. The degree of hardening and the kinetics of the hardening process are also important elements of reactivity. Some ACPs are more reactive than others. An ACP is considered "highly reactive" if it undergoes hardening in conjunction with conversion to a PCA material in the presence of a weak promoter, such as dicalcium phosphate dihydrate ("DCPD") with a grain size distribution containing a significant fraction of grain greater than 100 $\mu$m. Preferred highly reactive ACPs produce a hardened PCA material in the presence of weakly promoting DCPD and water at 37° C. in less than twelve hours, with hardening being substantially complete in about one to five hours, and ideally 10–30 minutes.

SUMMARY OF THE INVENTION

The present invention provides a synthetic, poorly crystalline apatitic (PCA) calcium phosphate material that has excellent biocompatibility, resorbability, and processability characteristics. The PCA calcium phosphate of the present invention is useful as a scaffold in any of a variety of in vivo and in vitro cell seeding applications.

The synthetic PCA material of the present invention is prepared in a two-step process in which i) at least one amorphous calcium phosphate (ACP) is exposed to a promoter in the presence of a limited amount of aqueous solution (preferably buffered to ensure compatibility with living cells), so that a hydrated precursor is formed; and ii) the hydrated precursor is allowed to harden, with concomitant conversion of the ACP (and any other reactants) to the synthetic PCA material. The reaction conditions employed to form the PCA material of the present invention are mild, so that the material (in either hydrated or hardened form) is compatible with living cells. Cells may be introduced into the material either at the hydrated precursor stage or after the material has hardened.

The PCA material of the present invention is strongly resorbable in vivo. At least 80% of the total mass of PCA material implanted intramuscularly or subcutaneously is resorbed within one year. More preferably, the PCA material is formulated so that at least 80% of an implant comprising at least 1 g of material, and preferably at least 1–5 g of material, is resorbed within one year. Still more preferably, the PCA material is formulated so that such an implant is resorbed within 9 months, 6 months, 3 months, or, ideally, 1 month. It will be appreciated, however, that resorption is related to surface area, so that the observed resorption of the inventive PCA material may vary according to the conformation of the material (e.g., as a disc, rod, plate, or other three-dimensional structure).

The PCA material of the present invention is highly formable and processable, particularly at the hydrated precursor stage, which is typically formulated as a paste or putty. The material may be formed into any of a variety of useful shapes, before or after cell seeding, and can be delivered to the site of use by any of a variety of methods. For in vivo applications, the material may be hardened in vitro (preferably at an elevated temperature—at or above about 37° C.) and subsequently introduced into an animal or human subject, e.g., by surgical implantation. Alternatively, the PCA material may be introduced into the body in hydrated precursor form and allowed to harden in situ. In preferred embodiments, the PCA material of the present invention substantially hardens in vivo within 15–40 minutes.

The present invention therefore provides therapeutic, structural, or cosmetic implants comprising the inventive PCA material and at least one cell. Preferably, the at least one cell is a bone-forming or bone-degrading cell. Particularly useful cell types include chondrocytes, osteocytes, osteoblasts, osteoclasts, mesenchymal stem cells, fibroblasts, muscle cells, hepatocytes, parenchymal cells, cells of intestinal origin, nerve cells, and skin cells, and may be provided as primary tissue explants, preparations of primary tissue explants, isolated cells, cell lines, transformed cell lines, and host cells. The implants may also comprise additional components such as biologically active agents or factors that alter the characteristics (such as resorbability, strength, adherence, injectability, frictional characteristics, etc.).

The invention also provides methods of preparing such implants; methods of growing bone or cartilage in vivo or in vitro, at natural sites or ectopic sites; methods of osseous augmentation; and methods of diagnosing disease states by assaying tissue-forming potential of cells isolated from a host. The invention also provides in vitro cell culture systems and cell encapsulation matrices.

DESCRIPTION OF THE DRAWINGS

FIG. 10 presents photomicrographs of tibial defects either untreated (10a) or treated (10b) with a PCA material of the present invention.

DETAILED DESCRIPTION OF PREFERRED EMBODIMENTS OF THE INVENTION

The PCA Material

The PCA material of the present invention is described in co-pending applications U.S. Ser. No. 08/650,764 and/or U.S. Ser. No. 08/446,182, each of which is incorporated herein by reference. The material is also described in a set of related applications, entitled "Delivery Vehicle"; "Conversion of Amorphous Calcium Phosphate to Form a Novel Bioceramic"; "Orthopedic and Dental Ceramic Implants"; and "Bioactive Ceramic Composites", each of which is on even date herewith and is incorporated herein by reference. In light of the breadth of disclosures in each of these related applications, the details of the inventive PCA materials will not be belabored here. A summary of its characteristics will suffice.

Figure 7:
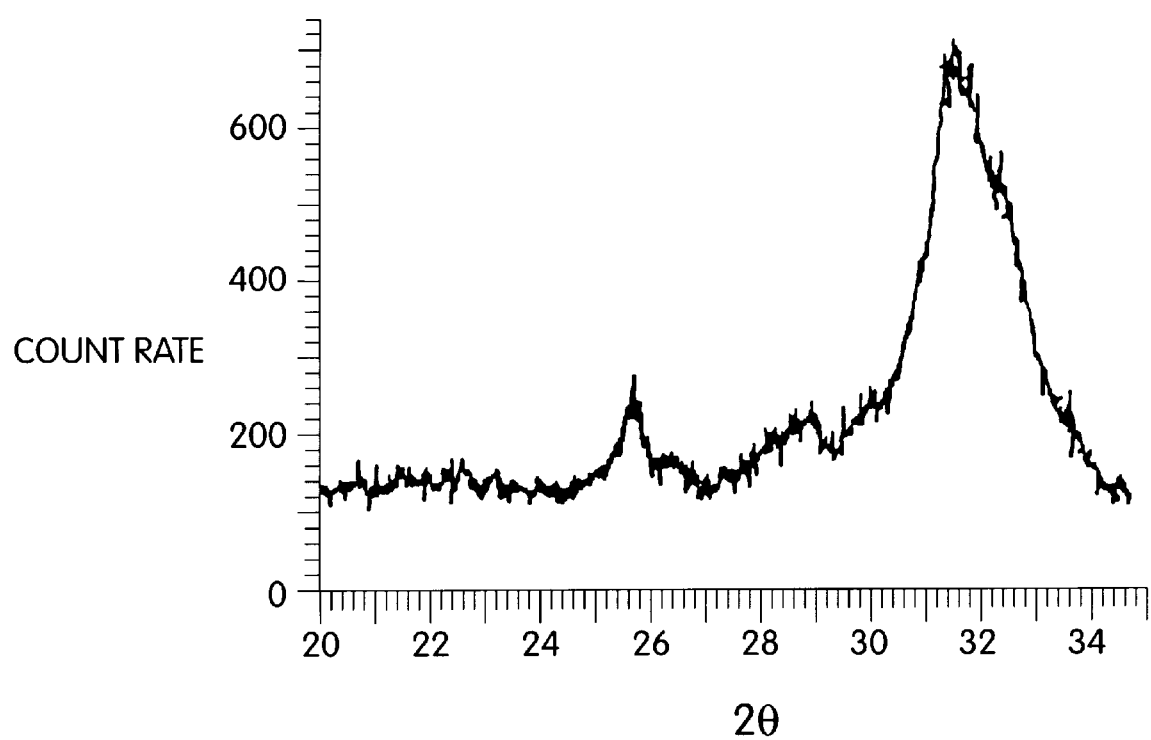
FIG. 7 is an X-ray diffraction pattern of naturally occurring bone.

The PCA material of the present invention is characterized by a distinctive X-ray diffraction pattern that reveals its poor crystallinity (see FIG. 7). Furthermore, the material has a calcium to phosphate ratio within the range of about 1.1 to 1.9, and preferably within the range of about 1.3–1.5. Thus, the PCA material of the present invention has characteristics that resemble those of natural bone and differ from those of other known calcium phosphate ceramics. These features make the PCA material of the present invention particularly suitable for use in orthopaedic and dental applications, as well as in other applications described herein.

As described in the above-referenced prior and related patent applications, the PCA material of the present invention is prepared by converting an amorphous calcium phosphate (ACP) into the PCA material. The first step of this conversion involves exposing the ACP to a promoter in the presence of a limited amount of aqueous solution so that a hydrated precursor having paste or putty form is produced. The hydrated precursor hardens and becomes the PCA material of the invention.

Where the PCA material of the invention is to be utilized in a cell seeding application, the hydrated precursor is preferably prepared with an aqueous solution that is a physiological medium. Examples of such media are well known in the art (e.g., Dulbecco's minimal essential medium; phosphate buffered saline; and carbonate, TRIS, or HEPES-buffered solutions); and those of ordinary skill are aware of particular media that are compatible with desired cell types.

Of course, it is not essential that the hydrated precursor be prepared with a buffered aqueous solution rather than water. However, as it is desirable to maintain cell viability, a hydrated precursor or hardened PCA material that has been prepared using water (or other minimal aqueous solution) will preferably be exposed to growth medium prior to, or at least coincident with, its exposure to cells. Introduction of a material into an animal can constitute exposure of the material to growth medium (and to cells).

The PCA material of the present invention may be prepared with any of a variety of additives, and/or may be prepared as a composite. For examples of desirable PCA material composites, see U.S. application entitled "Bioactive Ceramic Composites" and filed on even date herewith; for examples of biologically active materials that can be incorporated into the PCA material before or after cell seeding, see U.S. application entitled "Delivery Vehicle" and filed on even date herewith. In some cases, it will be particularly desirable to add factors to the PCA material that can affect cell growth, differentiation, and/or localization. For example, lamin, fibronectin, collagen, matrigel and its components, and other growth factors and extracellular matrix components.

Cells

The PCA material of the present invention may be seeded with any of a variety of cells. A "cell", according to the present invention, is any preparation of living tissue, including primary tissue explants and preparations thereof, isolated cells, cells lines (including transformed cells), and host cells. Preferably, autologous cells are employed, but xenogeneic, allogeneic, or syngeneic cells are also useful. Where the cells are not autologous, it may be desirable to administer immunosuppressive agents in order to minimize rejection. In preferred embodiments, such agents may be included within the seeded composition to ensure effective local concentrations of the agents and to minimize systemic effects of their administration. The cells employed may be primary cells, explants, or cell lines, and may be dividing or non-dividing cells. Cells may be expanded ex-vivo prior to introduction into the inventive PCA material. Autologous cells are preferably expanded in this way if a sufficient number of viable cells cannot be harvested from the host.

Any preparation of living cells may be use to seed the PCA material of the present invention. For example, cultured cells or isolated individual cells may be used. Alternatively or additionally, pieces of tissue, including tissue that has some internal structure, may be used. The cells may be primary tissue explants and preparations thereof, cell lines (including transformed cells), or host cells. Where the cells are host cells and are introduced into the inventive PCA material in vivo (see below), preferred sources of cells include, but are not limited to, the inner layer of the periosteum or perichondrium, blood or other fluids containing the cells of choice, and damaged host tissue particularly bone or cartilage) that includes such cells.

Any available methods may be employed to harvest, maintain, expand, and prepare cells for use in the present invention. Useful references that describe such procedures include, for example, Freshney, *Culture of Animal Cells: a Manual of Basic Technique,* Alan R. Liss Inc., New York, N.Y., incorporated herein by reference.

The PCA material of the invention is useful as a scaffold for production of hard or soft tissues. Tissue-producing or -degrading cells that may be incorporated into the material include, but are not limited to, chondrocytes, osteocytes, osteoblasts, osteoclasts, mesenchymal stem cells, other bone- or cartilage-producing cells or cell lines, fibroblasts, muscle cells, hepatocytes, parenchymal cells, cells of intestinal origin, nerve cells, and skin cells.

Methods of isolating and culturing such tissue-producing or -degrading cells, and/or their precursors, are known in the art (see, for example, Vacanti et al., U.S. Pat. No. 5,041,138; Elgendy et al., *Biomater.* 14:263, 1993; Laurencin et al., *J. Biomed. Res.* 27:963, 1993; Freed et al., *J. Cell. Biochem.* 51:257, 1993; Atala et al., *J. Urol.* 150:745, 1993; Ishaug et al., *J. Biomed. Mater. Res.* 28:1445, 1994; Chu et al., *J. Biomed. Mater. Res.* 29:1147, 1995; Thomson et al., *J. Biomater. Sci. Polymer Edn.* 7:23, 1995, each of which is incorporated by reference).

For example, mesenchymal stem cells, which can differentiate into a variety of mesenchymal or connective tissues (including, for example, adipose, osseous, cartilagenous, elastic, and fibrous connective tissues), can be isolated, purified, and replicated according to known techniques (see Caplan et al., U.S. Pat. No. 5,486,359; Caplan et al., U.S. Pat. No. 5,226,914; Dennis et al., *Cell Transplantation* 1:23, 1992, each of which is incorporated herein by reference). Such mesenchymal cells have been studied in association with tricalcium phosphate and hydroxyapatite carriers and have been found to be capable of successful differentiation from within such carriers (see Caplan et al., U.S. Pat. No. 5,197,985, incorporated herein by reference). Similar procedures are employed to direct mesenchymal cell differentiation within PCA material scaffolds of the present invention.

Of course, the present invention is not limited to the use of tissue-producing cells. Certain preferred embodiments of the invention utilize such cells, primarily because the inventive PCA material is so well suited to tissue-regeneration applications (particularly with those involving growth of bone and/or cartilage). Any cell may be seeded into the PCA material of the invention. In some cases, it will be desirable to include other cells in addition with tissue-producing cells.

The cells that are seeded into the inventive PCA material may be genetically engineered, for example to produce a protein or other factor that it useful in the particular application. In preferred embodiments, cells may be engineered to produce molecules that impart resistance to host immune attack and rejection. The Fas-L and CR-1 genes are examples of useful such genes.

Other Components

The PCA material scaffold employed in the present invention may include other components in addition to the PCA calcium phosphate itself and the cells seeded therein. For example, the PCA material may be formed as a composite with another material, preferably also biocompatible and/or resorbable, as described in U.S. application entitled "Bioactive Ceramic Composites" and filed on even date herewith.

Alternatively or additionally, one or more additives may be introduced into the PCA material before or after seeding. In certain preferred embodiments of the invention, one or more biologically active agents is incorporated into the PCA material. For discussion of such biologically active agents and their use in conjunction with the inventive PCA material, see U.S. application entitled "Delivery Vehicle" and filed on even date herewith.

Preferred biologically active agents for use in the seeded PCA material compositions of the present invention include factors that influence cell growth, differentiation, migration, and/or localization. For example, bone matrix contains a variety of protein factors that influence cell behavior (see, for example, Hubbell, *Bio/Technology* 13:565, 1995; Caplan et al., U.S. Pat. No. 4,609,551; Caplan et al., U.S. Pat. No. 4,620,327).

Also, cell matrix components can play important roles in division, differentiation, migration, and localization (see, for example, Hubbell, *Bio/Technology* 13:565, 1995). It may therefore be desirable to localize such matrix components within the seeded PCA material of the present invention. However, many of the functions achieved by association between cells and cell matrix components (e.g., definition of cell shape, achievement of cell polarity and organization, etc.) may well be accomplished by cell attachment directly to the inventive PCA material.

Other biologically active agents that are preferred for use in certain embodiments of the invention include nutrients, angiogenic factors, compounds that enhance or allow ingrowth of the lymphatic network or nerve fibers, etc. Immunomodulatory factors, and particularly inhibitors of inflammation, may be included where it is desirable to inhibit a host response to the implanted composition. Drugs may also be included (see U.S. Patent application entitled "Delivery Vehicle" and filed on even date herewith).

Introducing Cells into the PCA Material

Generally, cells are introduced into the PCA material of the present invention in vitro, although in vivo seeding approaches are employed in some circumstances (see below). Cells may be mixed with the hydrated precursor paste or putty prior to hardening or, alternatively, may be introduced into the PCA material composition after it has hardened. In either case, it is important that adequate growth (or storage) medium be provided to ensure cell viability. If the composition is to be implanted for use in vivo after in vitro seeding, sufficient growth medium must be supplied to ensure viability throughout, and for a short time following, the implant proceeding. Once the composition has been implanted, the porous nature of the PCA material allows the cells' nutritional requirements to be met by the circulating fluids of the host.

We have found Dulbecco's minimal essential medium to be particularly useful in the practice of the present invention. Other solutions that may be employed include, but are not limited to, phosphate-buffered saline; carbonate-, HEPES-, or TRIS-buffered solutions. In some cases, additional growth-stimulating components, such as serum, growth factors, amino acid nutrients, sugars, and salts, may be added to the aqueous solution employed in the present invention. However, it is generally desirable to avoid additives, as they can alter the hardening process of the inventive PCA material. If a particular collection of additives were selected to be used but had negative effects on PCA material characteristics, the precise PCA formulation can be varied and tested for its ability to satisfy hardening parameters in the presence of the additives.

Any available method may be employed to introduce the cells into the PCA material. In many cases, it will be desirable to introduce the cells into the hydrated precursor, before hardening. For example, cells may be injected into the hydrated precursor (preferably in combination with growth medium), or maybe introduced by other means such as pressure, vacuum, or osmosis. Alternatively (or additionally), cells may be layered on the hydrated precursor, or the hydrated precursor may be dipped into a cell suspension and allowed to remain there under conditions and for a time sufficient for cells to impregnate the material. Generally, it is desirable to avoid excessive manual manipulation of the cells in order to minimize cell death during the impregnation procedure. For example, in most situations it will not be desirable to manually mix or knead the cells with the PCA material paste; however, such an approach is perfectly useful in those cases in which a sufficient number of cells will survive the procedure. Cells may also be introduced into the hydrated precursor in vivo simply by placing the material in the body adjacent a source of desired cells. In some cases, it may be desirable to enhance such in vivo cell impregnation by including within the material an appropriate chemotactic factor, associative factor (i.e., a factor to which cells bind), or factor that induces differentiation of cells into the desired cell type.

Rather than being introduced into the hydrated precursor, cells may be introduced into the PCA material of the invention after it has hardened. Because the material is porous, cells are able to readily migrate into it. Cells may be introduced into the hardened PCA material by any available means. For example, cells may be layered on the material, or may be introduced by pressure, vacuum, or osmosis. Alternatively (or additionally), the hardened material may be placed in a cell suspension and maintained there under conditions and for a time sufficient for the cells to impregnate the material. Furthermore, the hardened PCA material may be prepared with a mold or-as a composite with a leachable material (e.g., sugars, salt crystals, or enzyme-degradable fillers) to provide seeding chambers or areas within the device. In such approaches, the cells are preferably introduced into these chambers through a pipette or a syringe. Cells may also be introduced into the inventive hardened PCA material in vivo, by placing the material in the body adjacent to a source of desirable cells or cell precursors as described above for the hydrated precursor. In preferred embodiments, the hardened material is placed adjacent the periosteum or perichondrium, or is exposed to blood, fluids, or damaged host tissue that contains the desirable cells.

As those of ordinary skill will readily appreciate, the number of cells to be introduced into the inventive material (be it the hydrated precursor or the hardened PCA material) will vary based on the intended application of the seeded material and on the type of cell used. Where dividing autologous cells are being introduced by injection into the hydrated precursor, use of 20,000–1,000,000 cells per $cm^3$ are expected to result in cellular proliferation and extracellular matrix formation within the material. Where non-dividing cells are employed, larger numbers of cells will generally be required. In those cases where seeding is accomplished by host cell migration into the material in vivo, exposure of the material to fluids containing cells (e.g., bone-forming cells), or to tissue (e.g., bone) itself has proven to be effective to seed the material with cells without the need for inoculation with a specified number of cells.

Applications

As alluded to above, the cell seeded PCA material of the present invention can be usefully employed in any of a variety of in vivo and in vitro systems. For example, the material may be used in bone tissue or repair applications or augmentation plastic therapy in vivo. Alternatively or additionally, the material may be employed as a cell encapsulation membrane or matrix. The material may also be utilized in artificial organ construction or repair.

In vitro, the material may be used as a three dimensional cell culture matrix, and as a model for analyzing osteoclast, osteoblast, chondrocyte, and/or macrophage cultures, progenitor cell differentiation, and/or reossification and calcium phosphate resorption. The material is particularly useful for tissue formation and/or degradation studies, for example employing cells such as progenitor cells, stem cells, osteocytes, osteoclasts, osteoblasts, chondrocytes, macrophages, myoblasts, and fibroblasts.

Certain preferred applications are discussed in more detail below, but the discussion is intended only for purposes of exemplification and is not intended to be limiting.

Bone Production and Healing

In preferred embodiments of the present invention, the PCA material is seeded with bone-forming cells or precursors thereof. Preferably, the PCA material is formulated, and the cell population is selected, so that the PCA material becomes ossified within a period of about 4–12 weeks.

In particularly preferred embodiments of the invention, the seeding is accomplished by placing the PCA material in contact with a source of the host's own bone-producing cells. Such cells are found in bone tissue or in bone-associated blood or fluids, including exogenous fluids that have been in contact with bone (including cancerous bone), bone materials, or bone regions such as the periosteum or the marrow.

Various modes of introducing the PCA material of the invention into bony sites are thoroughly described in U.S. application entitled "Orthopedic and Dental Ceramic Implants" and filed on even date herewith. Where the PCA material is to be implanted into a bony site in vivo in a manner that induces bleeding, such bleeding can effectively introduce bone-forming cells into the material so that no further seeding is required. Approaches that induce bleeding include those in which the PCA material is formed into a screw or pin, or is applied in conjunction with a screw or pin made from another material.

Where the PCA material is used as or in conjunction with a plate that opposes only cortical bone, it is preferred that a periosteal lesion be introduced in a manner that creates contact between the PCA material and the lesion, so that cells may penetrate into the PCA material from the lesion.

Similarly, in some embodiments of the invention, it will be useful to surgically prepare a PCA device seating within the bone by removing a portion of cortical bone at the implant site. Cells at the implant site will migrate into and seed the PCA material.

Of course, it is not required that the PCA material devices be seeded by in vivo impregnation of the host's own cells. Bone forming cells harvested from the host may be introduced in vitro into the device, so that a seeded composition is implanted in the host. Furthermore, seeding with non-autologous bone cells is also within the scope of the invention, but care must be taken to ensure that a desired amount of bone growth occurs prior to host rejection of the bone forming cells. Such non-autologous cells can be obtained from any of a variety of sources, including but not limited to primary sources, cell lines, and cell banks.

Bone formation in and around the PCA material can be enhanced by the incorporation of trophic factors and/or bone-growth inducing factors into, or onto, the PCA material device.

Osseous Augmentation

Seeded PCA compositions of the present invention are useful for the enhancement or alteration of the shape of bony structures (e.g., a chin). For such applications, the PCA material may be supplied either as a pre-hardened shape or a molded putty form and applied to a bony surface. Generally, PCA material formulations selected for augmentation applications will be those that resorb on a relatively slower time course, typically requiring 6–12 weeks for resorption.

PCA material employed in augmentation applications are typically seeded through application of cells or cell lines to the PCA material, although some preferred embodiments involve host cell seeding. The term "host cell seeding" encompasses any method by which cells of the host are introduced into the PCA material. For example, the term encompasses migration of host cells into a device implanted in vivo, as well as assisted migration accomplished by placing bone blood or fragments of the periosteum on or in contact with the device (in vivo or in vitro), among other things.

Cartilage Production and Healing

Damage to cartilage can result in serious physical deformations. Currently, the most common treatment for loss of cartilage is replacement with a prosthetic material, but many difficulties have been encountered with this approach. As put by one of the leaders in the field, "The lack of truly biocompatible, functional prostheses can have profound and tragic effects for those individuals who have lost noses or ears due to burns or trauma". Seeded PCA compositions of the present invention offer an attractive alternative in which the PCA material acts as a formable scaffold into and within which tissue can grow. The PCA material is bioresorbable so that, eventually, the PCA material implant can be replaced with natural tissue; the negative effects of long-term prosthetic implants can therefore be avoided.

The PCA material of the present invention can be seeded with cartilage-forming cells in order to optimize chondrogenesis. Preferably, this seeding is accomplished by placing the device in contact with a source of the host's own cartilage-forming cells (e.g., chondrocytes) or precursors thereto. Such cells are found in cartilage-associated blood or fluids, including exogenous fluids that have been in contact with cartilage or cartilagenous materials. Thus, fluids that have been in contact with the perichondrium, cartilage, or marrow typically contain such cells.

In many cases, e.g., a PCA material device designed for augmentation of a damaged ear, seeding can be accomplished by placing the PCA device in contact with the breached region of the perichondrium. In other cases, it will be useful to surgically prepare a seating for the PCA device within existing cartilagenous tissue by removing a portion of the cartilage at the implant site.

In some embodiments of the present invention, additional steps may be taken to augment chondrogenesis associated with the seeded PCA material. For example, cartilage-forming cells harvested from the patient may be introduced into the device in addition (or as an alternative to) cells that impregnate it after implantation in vivo. Alternatively or additionally, trophic factors or cartilage growth-inducing factors may be incorporated into or onto the device.

It should be clear that autologous cells are not required for the seeded PCA compositions employed in cartilage-forming applications; non-autologous cells are also within the scope of the invention so long as the cells are selected and the PCA material is formulated so that a desired amount of cartilage regeneration occurs prior to host rejection of the cartilage-forming cells. Thus, cells or tissues obtained from primary sources, cells lines, or cell banks are useful in the practice of this embodiment of the present invention.

Ectopic Bone or Cartilage Production

The seeded PCA material compositions of the present invention can be used to produce bone or cartilage formation at a site at which bone or cartilage does not normally occur. Introduction of a PCA composition into which bone- or cartilage-producing cells have been seeded into an in vivo implant site will result in bone or cartilage formation at that site. In preferred embodiments, the PCA material contains growth and/or trophic factors in addition to the seeded cells, so that maintenance of the ectopically-formed bone or cartilage can be prolonged. Once it has been produced, such ectopic tissue may either be left in place or may be surgically removed, depending on its intended use. Alternatively or additionally, trophic or growth factors external to the implant may be provided, e.g., through the use of encapsulated cells, polymer implants, or other method of factor delivery (see, for example, Aebischer et al., U.S. Pat. No. 4,892,538; Sefton, U.S. Pat. No. 4,353,888 and Winn et al. *Experimental Neurology* 140:126 (1996)).

Ectopic tissues may be formed in vitro using inventive seeded PCA material compositions. Preferably, a hydrated precursor is prepared, is shaped by hand or through the use of a mold or form, and is subsequently hardened at an elevated temperature (27–50° C.). Alternatively, the PCA material may first be hardened and subsequently be machined or otherwise formed into a desired shape. Cell seeding can be accomplished by any of the methods described herein, so that ectopic tissue will be formed in vitro in the desired shape. Generally, to ensure that the shape is maintained during cell growth, it will be desirable to inhibit the action of degredative enzymes and cells, as is known in the art.

Cell Encapsulation Matrix

The PCA material of the present invention provides an excellent growth matrix for use within the cell encapsulation environment. Use of this material can prevent cell settling, provide cell dispersion, and optimize nutrient localization by encapsulated cells. Thus, according to the invention, cells may be encapsulated within encapsulation devices in the presence of the hydrated precursor or hardened PCA of the present invention, and the resultant encapsulated devices may then be implanted in vivo for use in encapsulated cell therapy applications. Useful techniques for preparing and using cell encapsulation devices are described in, for example, Winn et al., *Expt. Neurol.* 140:126, 1996 and Aebischer, U.S. Pat. No. 4,892,538; Sefton, U.S. Pat. No. 4,353,888, and Kordower et al., *Cell Transplantation,* 14:155, 1995, each of which is incorporated herein by reference.

Research Applications

The PCA material of the present invention, due to its ease of preparation, mild formation conditions, sparing solubility in most aqueous systems, and tractability for use in cell-embedding applications, provides an attractive three-dimensional growth matrix for use in research and production tissue culture applications. Furthermore, the material is useful for tissue formation and/or degradation studies (e.g., of bone or cartilage). Preferably, the material employed in such studies in seeded with cells such as (but not limited to) progenitor cells, stem cells, osteocytes, osteoclasts, osteoblasts, chondrocytes, macrophages, myoblasts, and fibroblasts.

Diagnostics

Cell-seeded PCA materials of the present invention may be employed in diagnostics that detect various health or disease states. For example, the inventive PCA material can be used in qualitative or quantitative assays to determine the bone- or cartilage-forming potential of cells taken from a patient to be diagnosed. The inventive material can also be used in diagnostics to assay vascularization and hard tissue degradation. Various soft tissue diagnostics are also made possible with the inventive PCA material compositions.

EXAMPLES

Example 1

Preparation of Reactive Amorphous Calcium Phosphate

This example describes the step-by-step preparation and methods to render relatively inert amorphous calcium phosphate solids into a highly reactive amorphous calcium phosphate of the present invention.

Solution A was prepared at room temperature by the rapid dissolution of 55 g $Na_2HPO_4 \cdot 7H_2O$ (sodium phosphate), 50 g NaOH (sodium hydroxide), 30 g $NaHCO_3$, (sodium bicarbonate) and 2 g $Na_4P_2O_2 \cdot 10H_2O$ in 1.3 l of distilled water. Solution B was prepared at room temperature by rapid dissolution of 43 g $Ca(NO_3)_2 \cdot 4H_2O$ (calcium nitrate tetrahydrate) and 1 g $MgCl_2 \cdot 6H_2O$ in 0.5 l of distilled water.

The inert carbonated amorphous calcium phosphate was then prepared at room temperature by the rapid addition of solution B to rapidly stirring solution A. The precipitate of gel-like amorphous calcium phosphate thus formed was immediately filtered using filter paper (0.05 sq. m) with medium filter speed and a vacuum pressure of about $10^{-2}$ torr. The material formed a thin cake and was washed with approximately 4 liters of distilled water by adding water into the filtrating funnel. The washed material was then collected using spatula and immersed into a liquid nitrogen in a 2.5 L container. Following the formation of hard frozen pieces, the container was transferred into a vacuum chamber for 24 hrs ($10^{-1}$–$10^{-2}$ torr), until a fine and dry powder was obtained.

Although the procedure described above may be performed at room temperature, the entire process preferably takes place below ambient temperature (4–5° C.), so as to further prevent the amorphous state from converting into more stable crystalline form. Further, such elements or ions known to act as inhibitors of crystalline hydroxyapatite formation may be added into the solution in trace amounts.

An infrared spectrum of the inert amorphous material at this point in the process contains peaks characteristic of P—O groups (600 and 1000 $cm^{-1}$), $CO_3^{2-}$ group (1,420–1,450 $cm^{-1}$) with relatively large peak of O—H group (~3,550 $cm^{-1}$). X-ray diffraction pattern of the same material show amorphous nature of the material as demonstrated by absence of any sharp peaks when the measurement of crystallinity is determined by taking ratio of coherent peaks to background.

Figure 1:
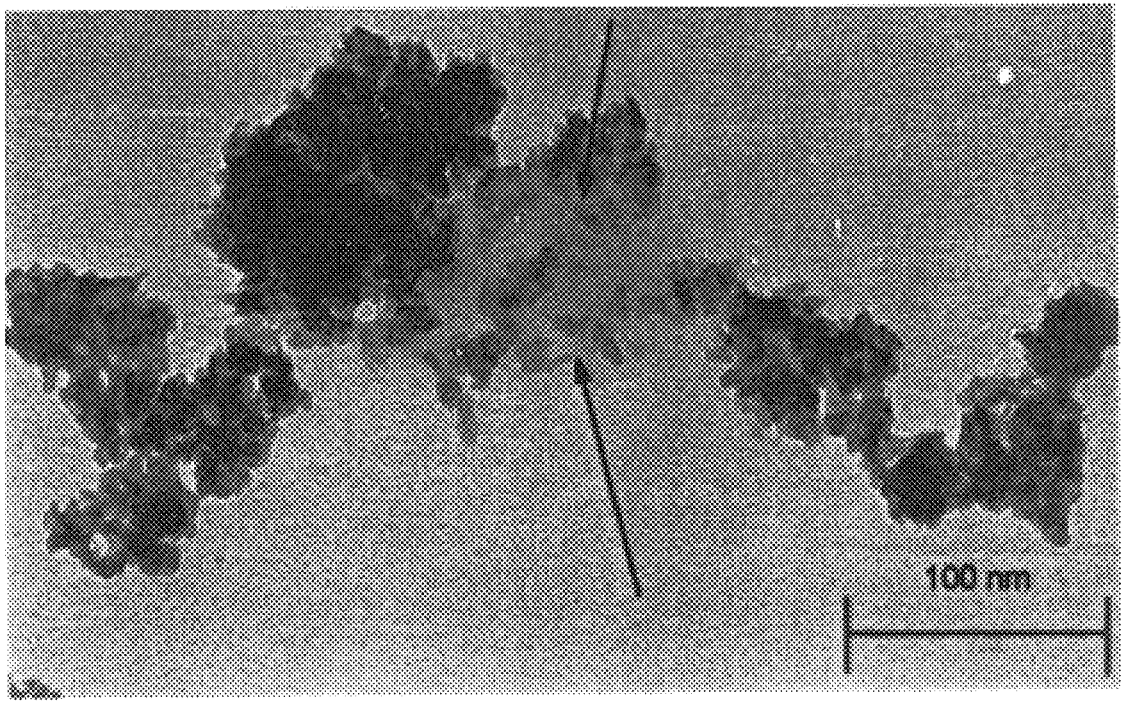
FIG. 1 is a high-resolution transmission electron micrograph of the reactive amorphous calcium phosphate illustrating the nanometer-sized grains in clusters with relatively unclear boundaries and partially immersed in shapeless form (arrows)
Figure 2:
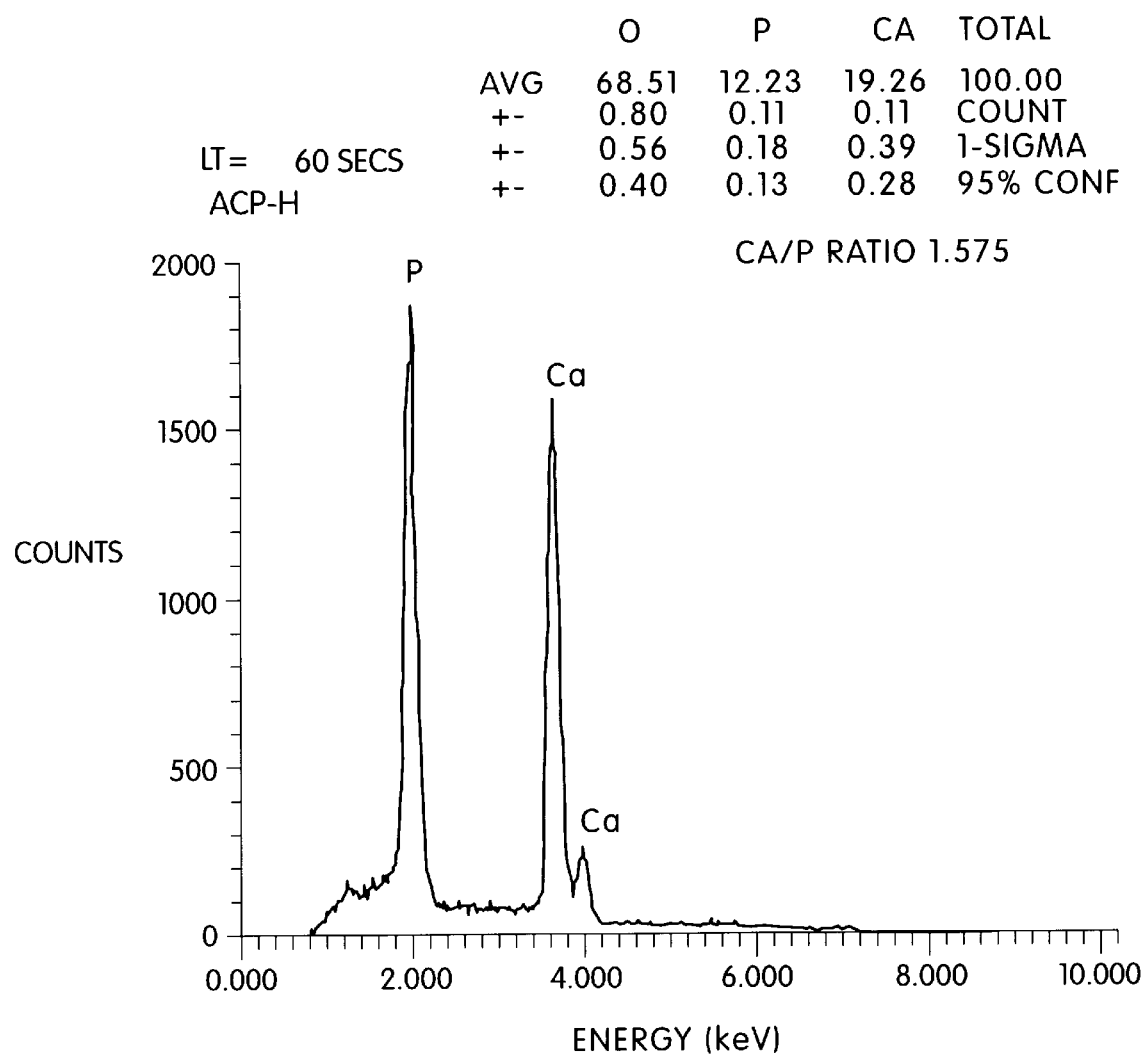
FIG. 2 is an energy-dispersive electron microprobe spectrum of the reactive amorphous calcium phosphate of the present invention after the vacuum heating procedure which yielded Ca/P to be 1.58.
Figure 4A:
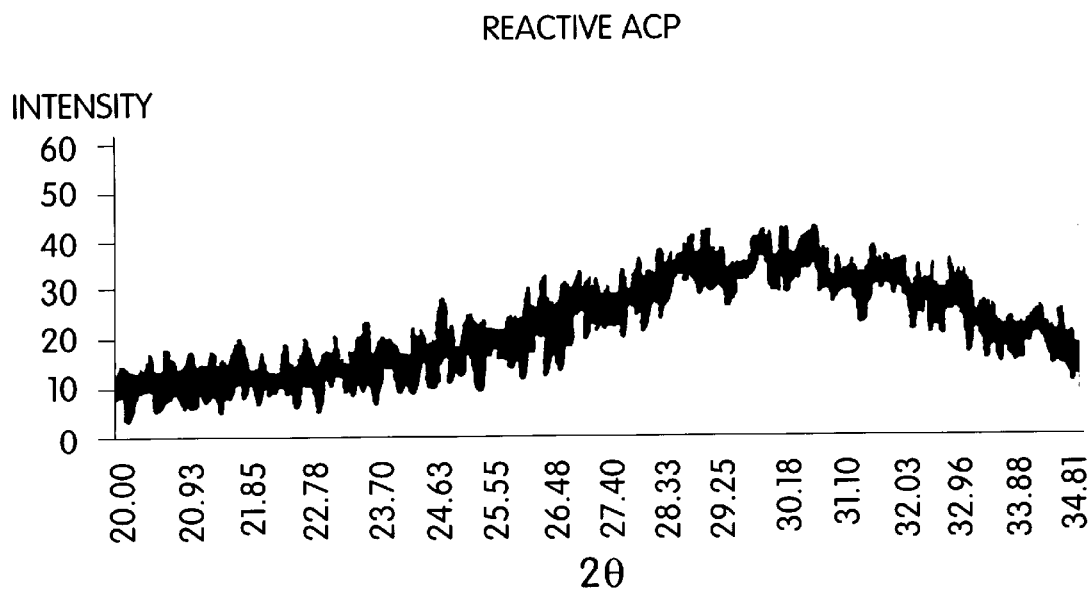
FIG. 4 are X-ray diffraction patterns of (a) reactive amorphous calcium phosphate; and (b) dicalcium diphosphate used in a reaction to form a bone substitute material of the invention.
Figure 4B:
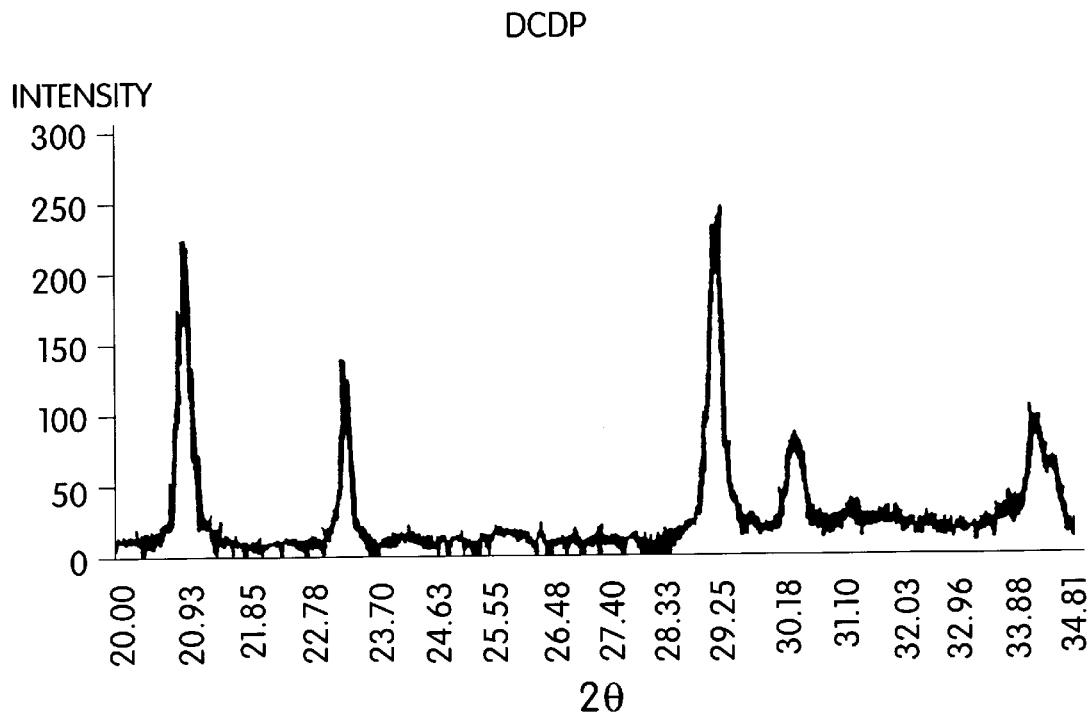

The inert amorphous material described above was then made into a reactive form by heating for 60 minutes at 450° C. (±3° C.). The IR of the heated material (not shown) shows reduction of particular O—H and $CO_3^{2-}$ groups, indicating significant reduction of $H_2O$ and $CO_3^{2-}$ as $CO_2$ and $H_2O$. In similarly prepared samples the carbon content was observed to drop approximately 60% with a total carbonate ratio decreasing from 1.56% to 0.5%. Note, however, that the amorphous nature of the material was not lost during this process, as demonstrated by the X-ray diffraction pattern shown in FIG. 4(*a*). The Ca/P ratio measurement of this material after the heat treatment was determined to be 1.575, using a method of quantitative electron microprobe analysis (FIG. 2). The overall morphological and ultrastructural properties of amorphous material is shown in FIG. 1, as seen under a transmission electron microscope. Note the "amorphous" appearance of the material with absence of sharp edges separating each granules with certain portion of the material to exhibit shapeless form (arrows). An extremely high specific surface area of 120 $m^2/g$, with an average pore size of approximately 130 Å was observed in this material.

Example 2

Preparation of Reactive Amorphous Calcium Phosphate

The preparation was conducted as described in Example 1 above, with the exception that the preparation of Solutions A and B was replaced by the following reactions. Solution A was prepared at room temperature by the rapid dissolution of 90.68 g of $Ca(NO_3)_2 \cdot 4H_2O$ in 1.2 liter of carbonated distilled $H_2O$. Solution B was prepared by dissolving 40.57 g of $K_2HPO_4$ in 1.53 liters of distilled $H_2O$, containing 24 ml of 45 vol. % KOH solution. Chemical and physical properties of the product amorphous calcium phosphate resulting from this procedure were similar to those of the material prepared accordingly for Example 1.

Example 3

Preparation of Reactive Amorphous Calcium Phosphate

The preparation was conducted as described in Example 1 above, with the exception that the preparation of Solutions A and B were replaced by the following reactions. Solution A was prepared at room temperature by the rapid dissolution of 10.58 g of $Ca(NO_3)_2 \cdot 6H_2O$ in 0.15 liters of carbonated distilled $H_2O$ at pH greater than 9.0, as adjusted by NaOH. Solution B was prepared by dissolving 7.8 g of $(NH_4)_2HPO_4$ in 0.35 liters of distilled $H_2O$. Chemical and physical properties of the product amorphous calcium phosphate resulting from this procedure were similar to those of the material prepared according to Examples 1 and 2.

Example 4

Preparation of Synthetic Poorly Crystalline Apatitic Drug Delivery Material from Reactive Amorphous Calcium Phosphate This example describes the preparation of drug delivery vehicle material of the invention.

The dicalcium phosphate dihydrate (DCPD) used in this example was prepared in the following manner. Solution A was prepared at room temperature by rapid dissolution of 10 g $H_9N_2O_4P$ (diammonium hydrogen phosphate) in 500 ml distilled water at a pH of 4.6–4.8. Solution B was prepared at room temperature by the rapid dissolution of 17.1 g $Ca(NO_3)_2 \cdot 4H_2O$ (calcium nitrate tetrahydrate) in 250 ml distilled water. The dicalcium phosphate dihydrate was prepared at room temperature by the rapid addition of solution B to the stirring solution A. Immediately thereafter, the sample was filtered using filter paper (0.05 sq. m) with medium filter speed and a vacuum pressure of about $10^{-2}$ torr. The material formed a thin cake which was washed with about 2 liters of distilled water and then air dried at room temperature for 24–72 hrs.

The reactive amorphous calcium phosphate material prepared from Example 1 was physically dry-mixed with dicalcium phosphate dihydrate ($CaHPO_4 \cdot 2H_2O$) at 50:50 wt % using a mortar and pestle for 3–5 min. Water (1 ml/g of mixed material) was then added to the powder mixture to yield a paste-like consistency. The amount of $H_2O$ added varied, depending on whether a thick or thin paste was desired. The paste material was then wrapped in moist tissue paper and was hardened into a solid mass by heating 37° C. The hardening process could be delayed for several hours by wrapping the sample in parafilm and holding it at 4° C. Also, hardening can be allowed to proceed at ambient temperature, although setup times may then be expanded.

The hardened material was composed of nanometer-sized, poorly crystalline apatite calcium phosphate with an inherent solubility property that exceeded reported solubilities for a synthetic hydroxyapatite material. This is demonstrated in FIG. 3, where the concentration of calcium ions released into a controlled pH buffer solution over 24 hrs at 37° C., was significantly higher for the PCA material of the present invention (curve 50) than the standard crystalline hydroxyapatite material (curve 52).

Example 5

Preparation of Synthetic, Poorly Crystalline Apatitic Drug Delivery Material from Precursors of Selected Particle Size This example demonstrates the preparation of synthetic PCA drug delivery vehicle materials using precursors having a selected particle size.

DCPD was prepared as described in Example 4. The dry material was ground for 5 minutes in a SPEX 8510 laboratory mill with a SPEX 8505 alumina ceramic grinding chamber. Following grinding the material was serially sieved through a Tyler test sieve shaker to produce DCPD with 8 different grain size distributions as indicated in Table 1.

TABLE 1

DCPD Grains size distribution

Figure 8:
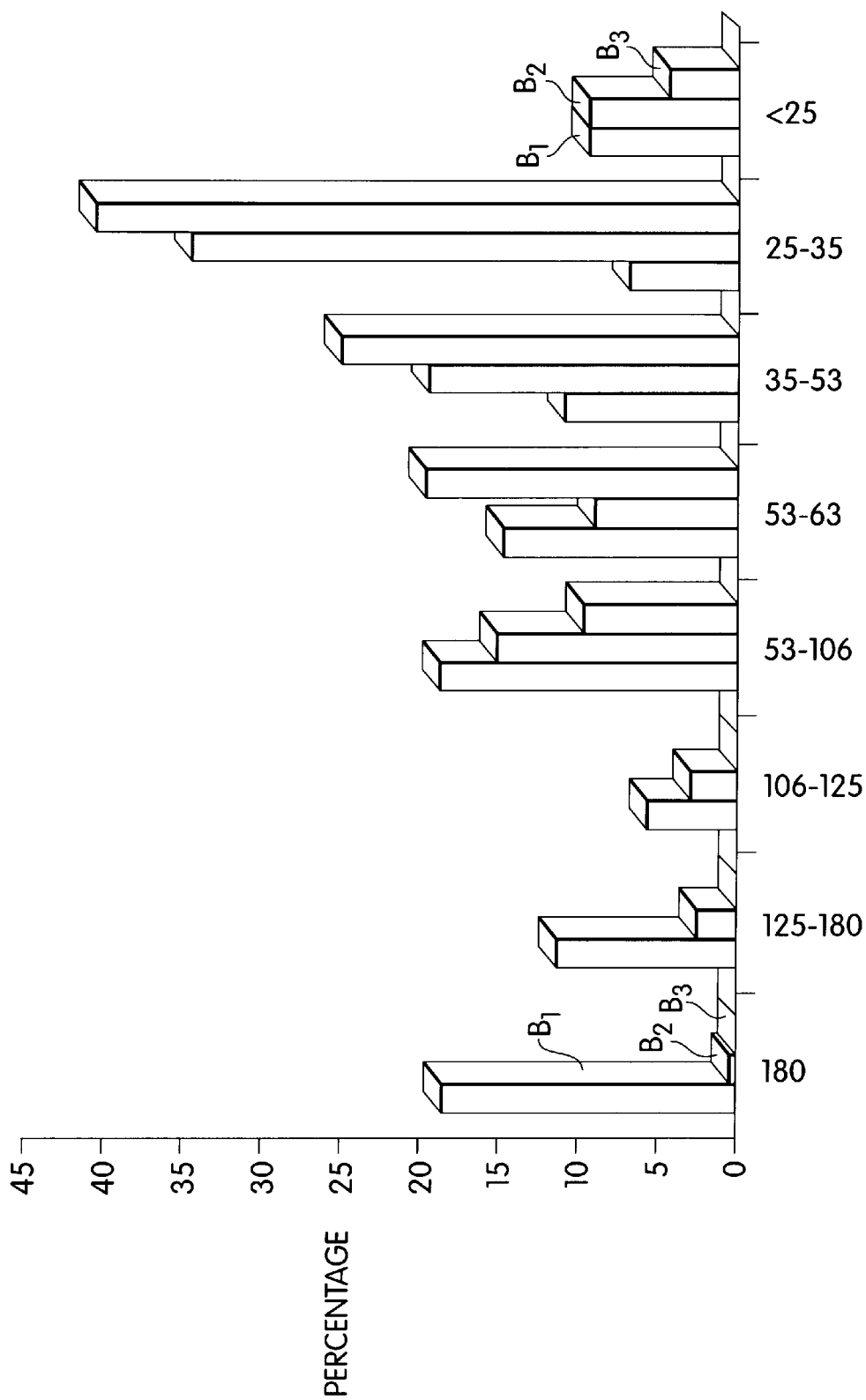
FIG. 8 is a bar graph displaying particle size distribution for various formulations described in Example 5.

| Sample | Grain Size Distribution |
|---|---|
| 1 | <25 μm |
| 2 | 25–35 μm |
| 3 | 35–53 μm |
| 4 | 53–63 μm |
| 5 | distribution B3 (FIG. 8) |
| 6 | 106–125 μm |
| 7 | distribution B2 (FIG. 8) |
| 8 | unsieved distribution B1 (FIG. 8) |

The reactive amorphous calcium phosphate material prepared from Example 1 was physically dry-mixed 1:1 (wt/wt) with DCPD for 10 minutes using a SPEX 8510 laboratory mill with a SPEX 8505 alumina ceramic grinding chamber. Water (1.0–0.8 ml/gm of dry mix) was then added to the powder mixture to yield a paste-like consistency. 5 of the 8 samples indicated in Table 1 hardened well in 30 minutes at 37° C. Samples 6, 7 and 8 did not harden as quickly or as firmly as the other samples. Each of these samples had significantly higher percentages of >100 μm particles than did the other samples.

Example 6

Figure 3:
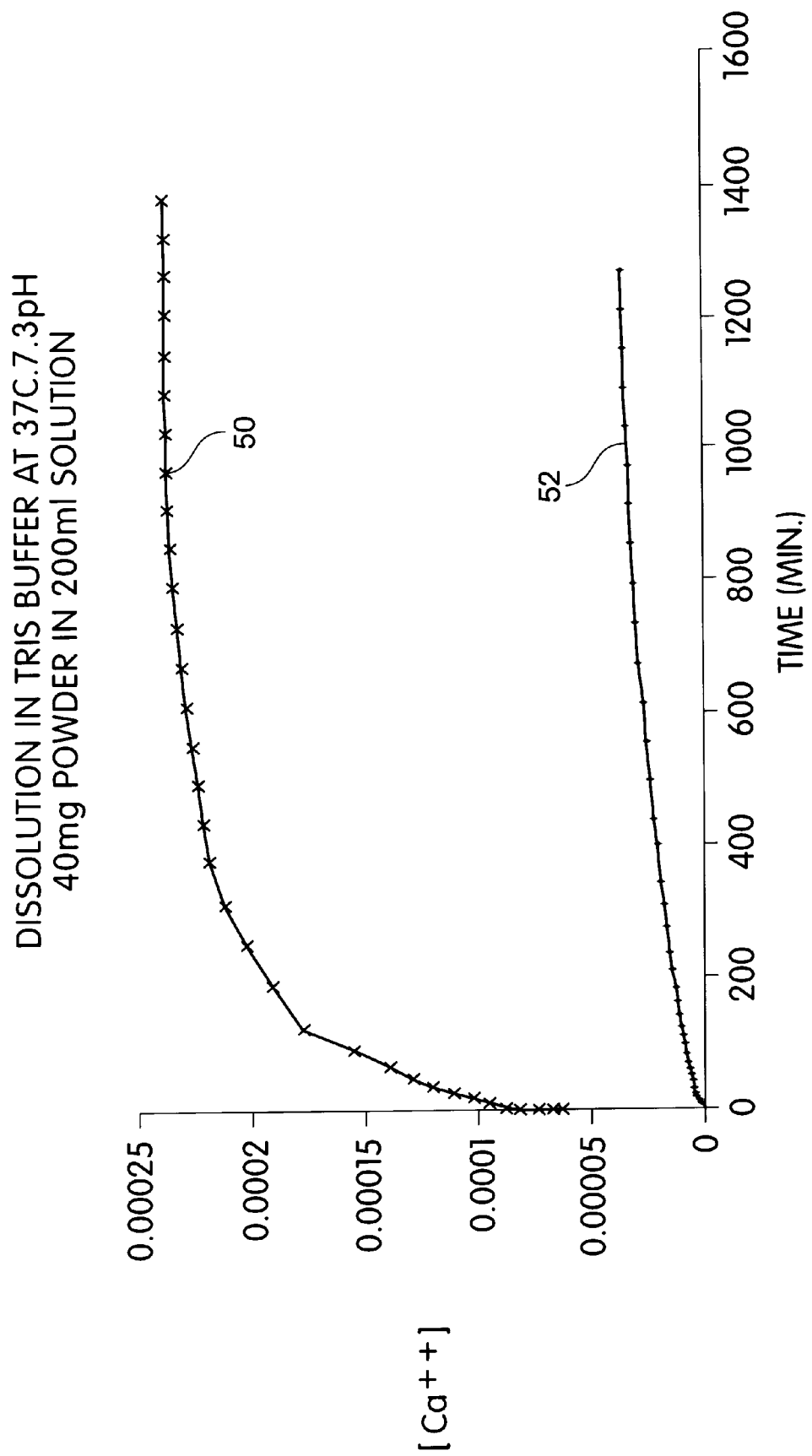
FIG. 3 is a solubility curve of a poorly crystalline apatitic calcium phosphate product derived from amorphous calcium phosphate of the present invention, as compared with a crystalline hydroxyapatite. Note the relative higher solubility of the material of the present invention versus a more crystalline form of hydroxyapatite, as measured by the amount of calcium ions released into solution at 37° C.

Preparation of Synthetic PCA Drug Delivery Material from Reactive Amorphous Calcium Phosphate Reactive amorphous calcium phosphate material as prepared in Examples 1 was dry-mixed with other calcium phosphate compounds, according to the method described in Example 4. These compounds included, but were not limited to: $Ca(PO_3)_2$ (calcium metaphosphates), $Ca_7(P_5O_{16})_2$ (heptacalcium decaphosphate), $Ca_2P_2O_7$ (calcium pyrophosphate), $Ca_3(PO_4)_2$ (tricalcium phosphates). The dry-mixture ratio was properly calculated to be between Ca/P ratios of 1.5–1.70, depending on the molar Ca/P ratio of the compound mixed with the reactive amorphous calcium. The resulting material was poorly crystalline apatitic calcium phosphate solids with solubility properties same as shown in FIG. 3.

Example 7

Preparation of an Injectable Paste for Formation of a Synthetic, PCA Material from a Reactive, Amorphous Calcium Phosphate This example describes the preparation of an injectable paste for the formation of poorly crystalline apatitic calcium phosphate solid.

The dried mixed materials prepared according to Examples 4 or 6 were mixed with distilled $H_2O$ (2.3 ml/g). A paste was formed that could be easily shaped by hand or injected through a nozzle as small as 0.5 mm ID. The flowability increased after refrigerating the paste at 4° C. for 2–3 hrs.

The material could be stored in a paste form for about 12 hours at 4° C. in an air tight container without hardening.

Example 8

Characteristics of a Synthetic Poorly Crystalline Apatitic Calcium Phosphate

The crystalline content of the PCA material was determined by X-ray diffraction.

FIG. 5a–d are the X-ray diffraction spectra of the reaction product between DCPD and the reactive amorphous calcium phosphate as described in Example 4. The reaction mixture was placed in a moist environment at 37° C. and examined by X-ray diffraction spectrometry at different times. X-ray scan conditions were (a) copper anode, (b) λ=1.4540598 Å, and (c) a scan range 20–35° at a step of 0.02° and step interval of 2 seconds. FIG. 6 shows the infrared spectra of dicalcium phosphate dihydrate (a), the activated ACP of the invention (b), and the PCA material of the present invention (c).

Figure 5A:
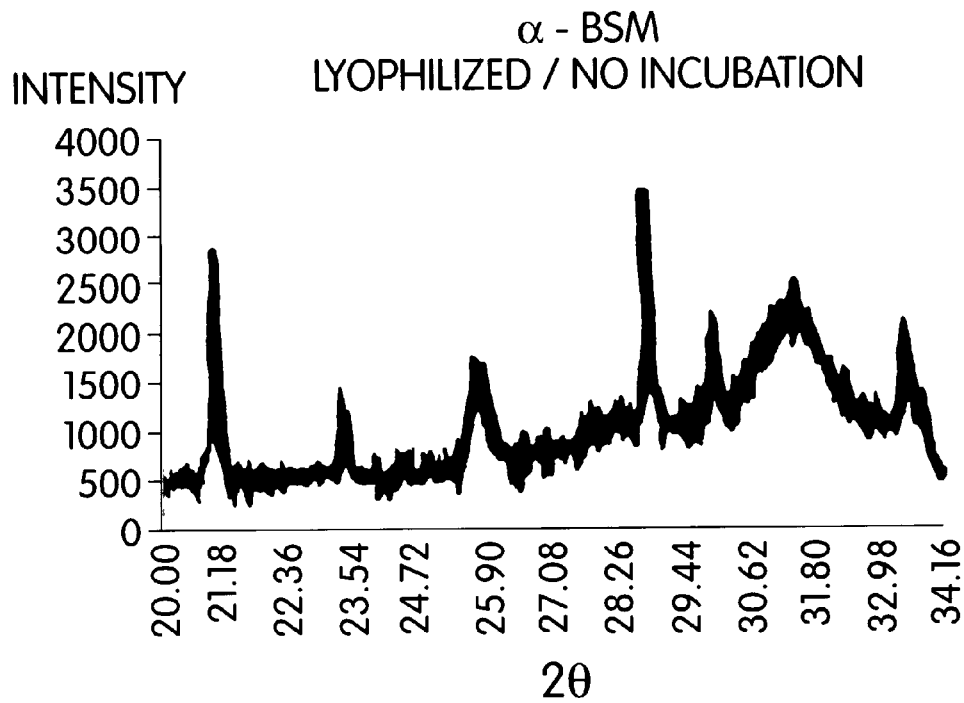
FIG. 5a–d are X-ray diffraction patterns tracking the progress of the reaction of a mixture of reactive amorphous calcium phosphate and dicalcium diphosphate to form a PCA material of the present invention.
Figure 5B:
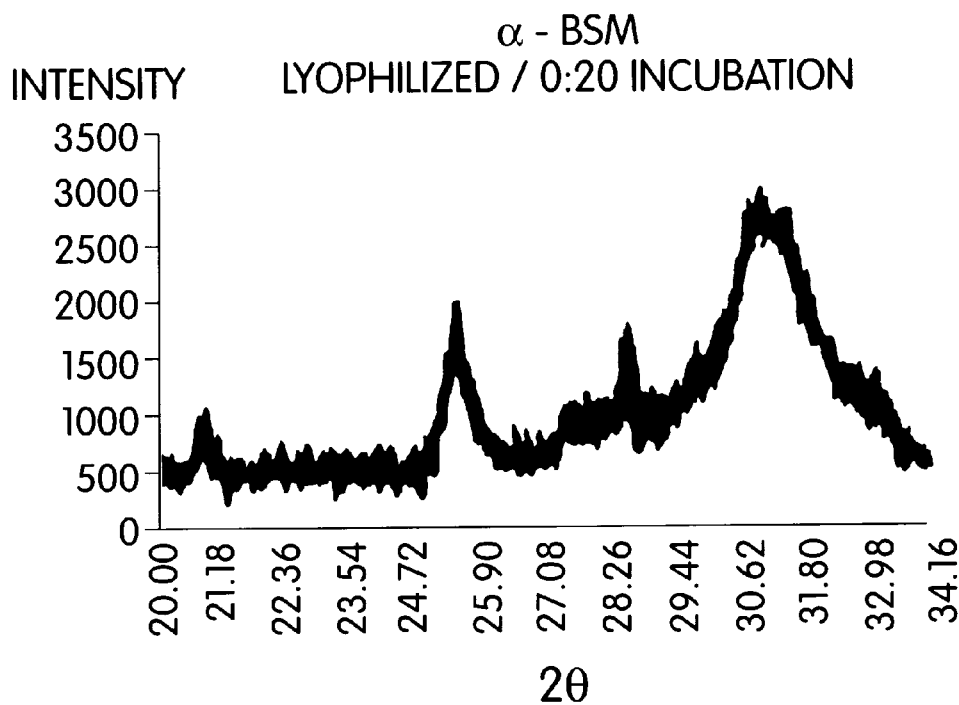
Figure 5C:
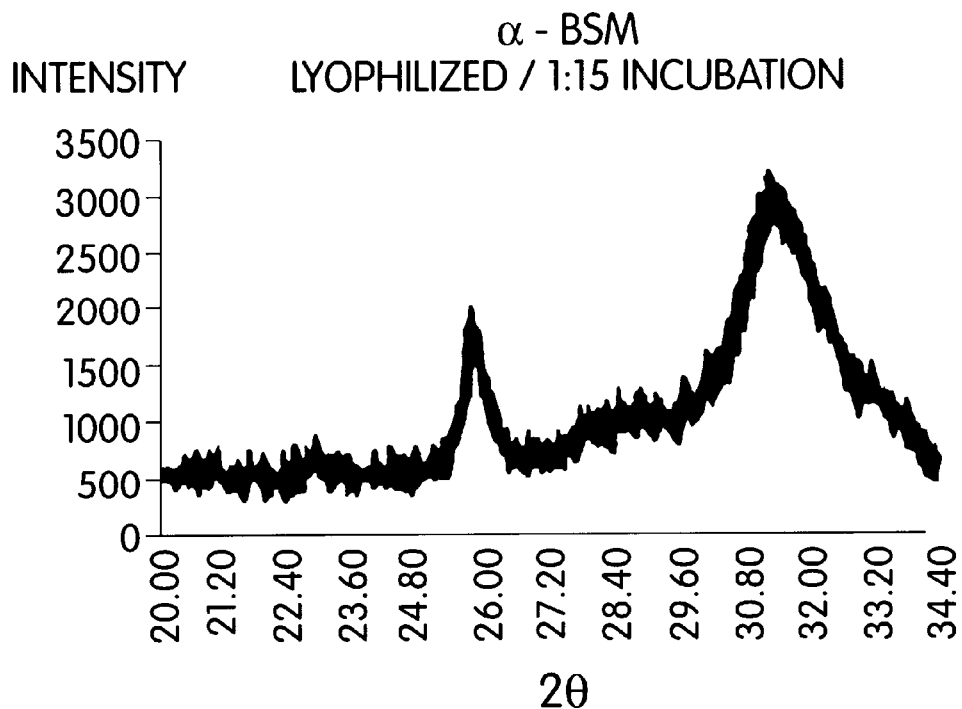
Figure 5D:
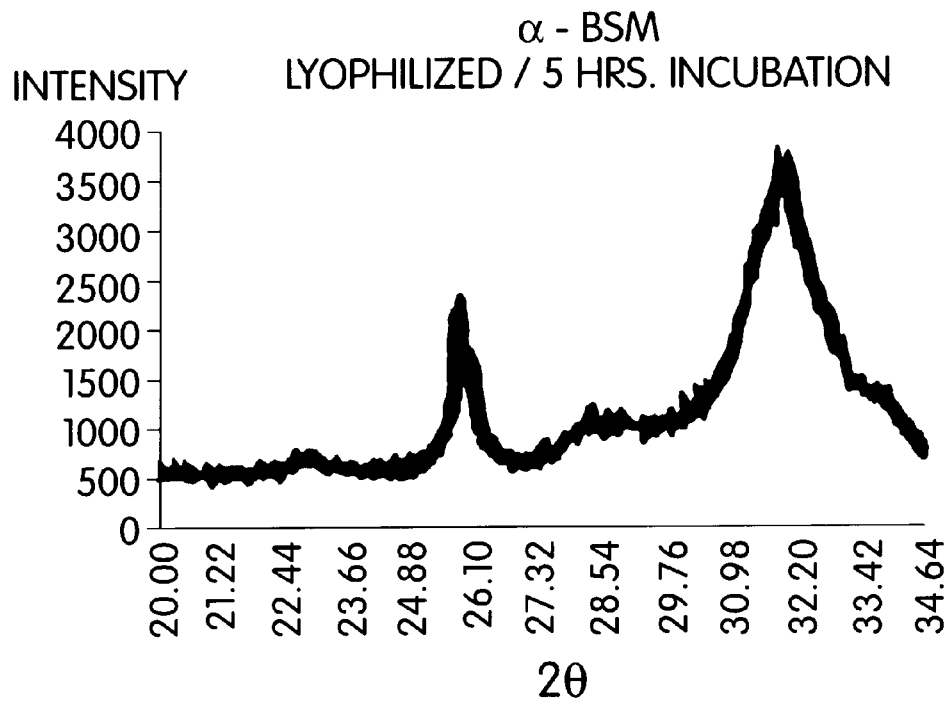
Figure 6A:
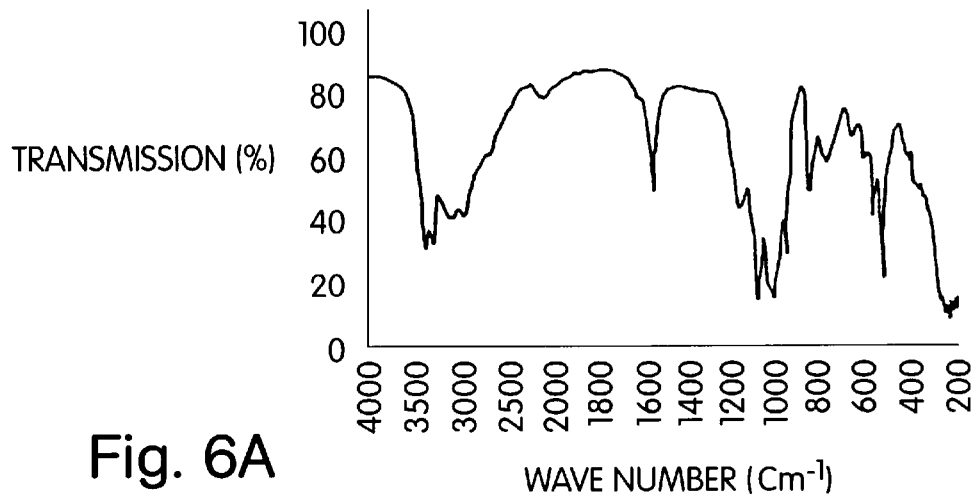
FIG. 6 is infrared spectra of (a) dicalcium phosphate dihydrate, (b) the activated ACP of the invention, and (c) the PCA material of the present invention.
Figure 6B:
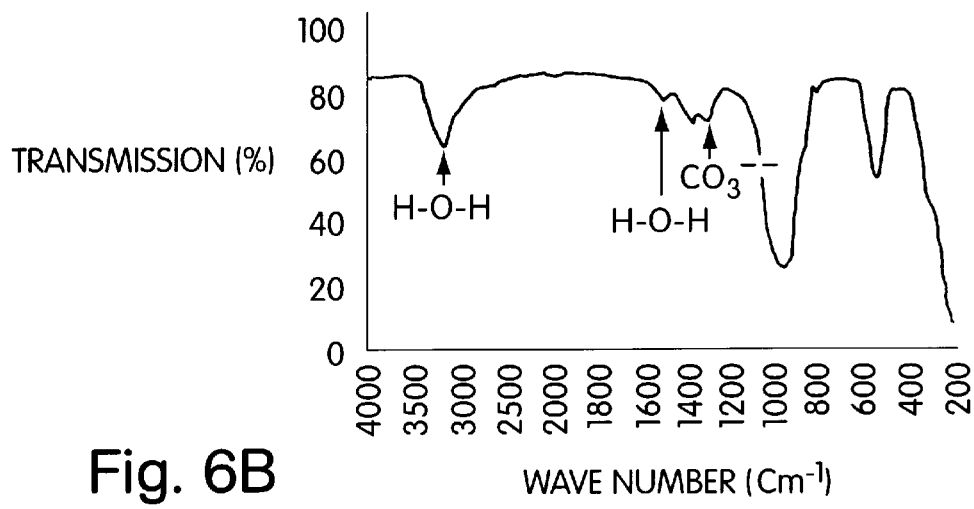
Figure 6C:
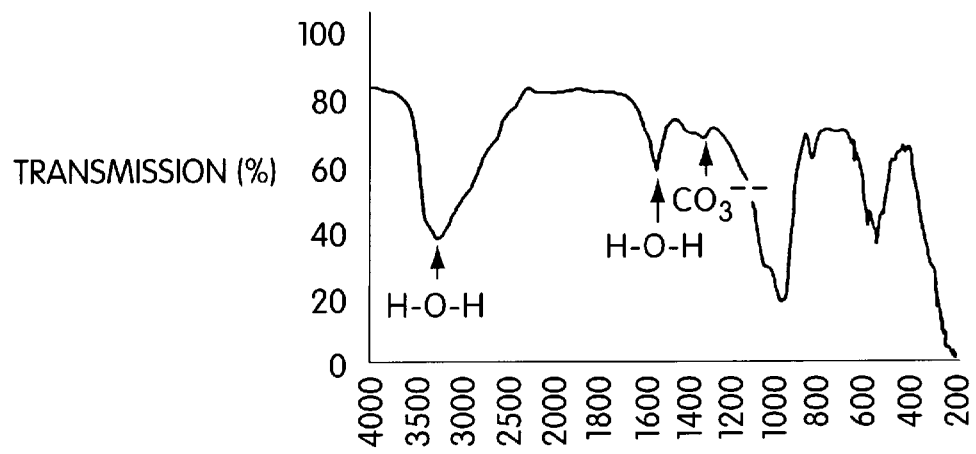

Samples of FIGS. 6a–6d were incubated for 0, 20 min, 75 min and 5 hours, respectively. The samples were removed at the noted time and lyophilized to preserve chemical characteristics. FIG. 5a, taken at the start of the reaction, represents a combination of peaks attributable to the starting ACP and dicalcium diphosphate (see, FIG. 4 for component XRD patterns). The sharp peaks at ca. 20.25°, 23.5°, 29.5°, 30.75° and 34.2° for crystalline dicalcium diphosphate are readily observed. With increase in reaction time, the sharp crystalline peaks subside and wide (amorphous) peaks appear centered at 26°, 28.5°, 32.0° and 33.0°. It is interesting to note that there is no significant change in the spectra after 75 minutes of reaction, indicating that the conversion reaction was essentially complete in little more than one hour. The X-ray diffraction pattern of the PCA material of the invention (FIG. 5d) can be compared to that of naturally occurring bone, shown in FIG. 7. The two spectra are nearly identical, indicating the close biomimetry of the apatitic calcium phosphate of the invention.

Examples 9–12

Characteristics of Injectable Paste for Formation of Synthetic PCA Material from a Reactive, Amorphous Calcium Phosphate These examples demonstrate the effect of fluid volume on the consistency and reactivity of injectable paste to be used in the formation of a synthetic, poorly crystalline hydroxyapatite material. Each of the pastes were prepared as described in Example 7, above, and the consistency and rate of reaction at room temperature and 37 °C. were determined. Observations are reported in Table 2.

TABLE 2

Formability, injectability and reactivity of one gram drug vehicle material prepared with variable water volume

| Example No. | water volume (mL) | formability | injectability | hardening time (min) (4° C./RT/37° C.) |
|---|---|---|---|---|
| 9 | 0.7 | – crumbles | – | –/–/– |
| 10 | 0.8* | +++ easily formed paste | + | >60/>60/30 |
| 11 | 0.9* | ++ toothpaste | ++ | >60/>60/30 |
| 12 | 1.0 | + liquid toothpaste | +++ | >60/>60/30 |

*Under some circumstances (e.g., evaporation) these samples may dry out somewhat over a period of one hour at room temperature. In such cases, additional water may be added to restore the original consistency.

Example 13

Infrared Spectra of Precursor and Product Materials

This example compares the infrared spectra of crystalline and amorphous precursors produced according to the Examples and the final PCA material produced by reacting similar precursors. FIG. 7a presents the IR spectrum of brushite (DCPD) prepared as described in Example 4; FIG. 7b presents the spectrum of ACP after heat treatment, prepared as described in Example 1; and FIG. 7c is the IR spectrum of the PCA material prepared as described in Example 4.

The purpose of this study was to assay resorption and ossification of PCA calcium phosphate in a bony implant site. The method is also useful for testing the resorption and ossification properties of PCA calcium phosphate formulations and composites of the invention.

The test article used was a PCA calcium phosphate formulation prepared as described in Example 4. The ACP and DCPD were mixed in the specified proportions and ground for 1 minute, 30 seconds in the SPEX grinder equipment.

Adult (>5 month old) NZW male rabbits were held in quarantine and acclimatized for a minimum of 10 days prior to the initiation of the study. Animals were individually housed in suspended stainless steel cages. Wood shavings were used in dropping pans under the cages. Prior to initiation of the study, animals were assigned to groups or treatments randomly and were identified by a numbered ear tattoo and by a corresponding cage card. All animals had single defects placed in one tibia. Timepoints for evaluations were 2, 4, and 8 weeks (2 animals at each timepoint). Surgery was performed under full anesthesia and aseptic surgical conditions.

After obtaining adequate anesthesia (e.g., ketamine/xylazine to effect), using aseptic technique, an incision was made over the lateral proximal tibia. The soft tissue was deflected away and the bone exposed. Using an approximately 5 mm trephine in a low speed dental handpiece with irrigation (0.9% physiologic saline) as needed, a ~5.5 mm diameter hole was cut through the cortical portion of the bone. The bony disk was dissected free from the cortex and the site was prepared for implantation. The hydrated precursor material in paste form was placed into the defect. Defects in control animals were left untreated. The soft tissues were then closed in layers. One sample per animal was prepared using this method.

Clinical observations of the animals' general health and well-being, with special regard to their ambulatory abilities, were made at least weekly. All animals appeared to be in good health. At the end of the study the animals were euthanized with an overdose of anesthetic and the implant site collected. Radiographs of the tibiae were made at scheduled intervals including after surgery and at the time of necropsy.

The implantation sites were fixed in formalin and stained with either hematoxylin and eosin, Masson's trichrome, or Von Kossa stained slides from decalcified samples. Undecalcified histological samples were also prepared and stained with light green basic fuschin. Slides were microscopically evaluated by a board certified veterinary pathologist (ACVP) with experience in laboratory animal pathology. Subjective observations were made of bone morphology, and presence or absence of organized bone and of detectable PCA calcium phosphate material was noted.

Figure 9:
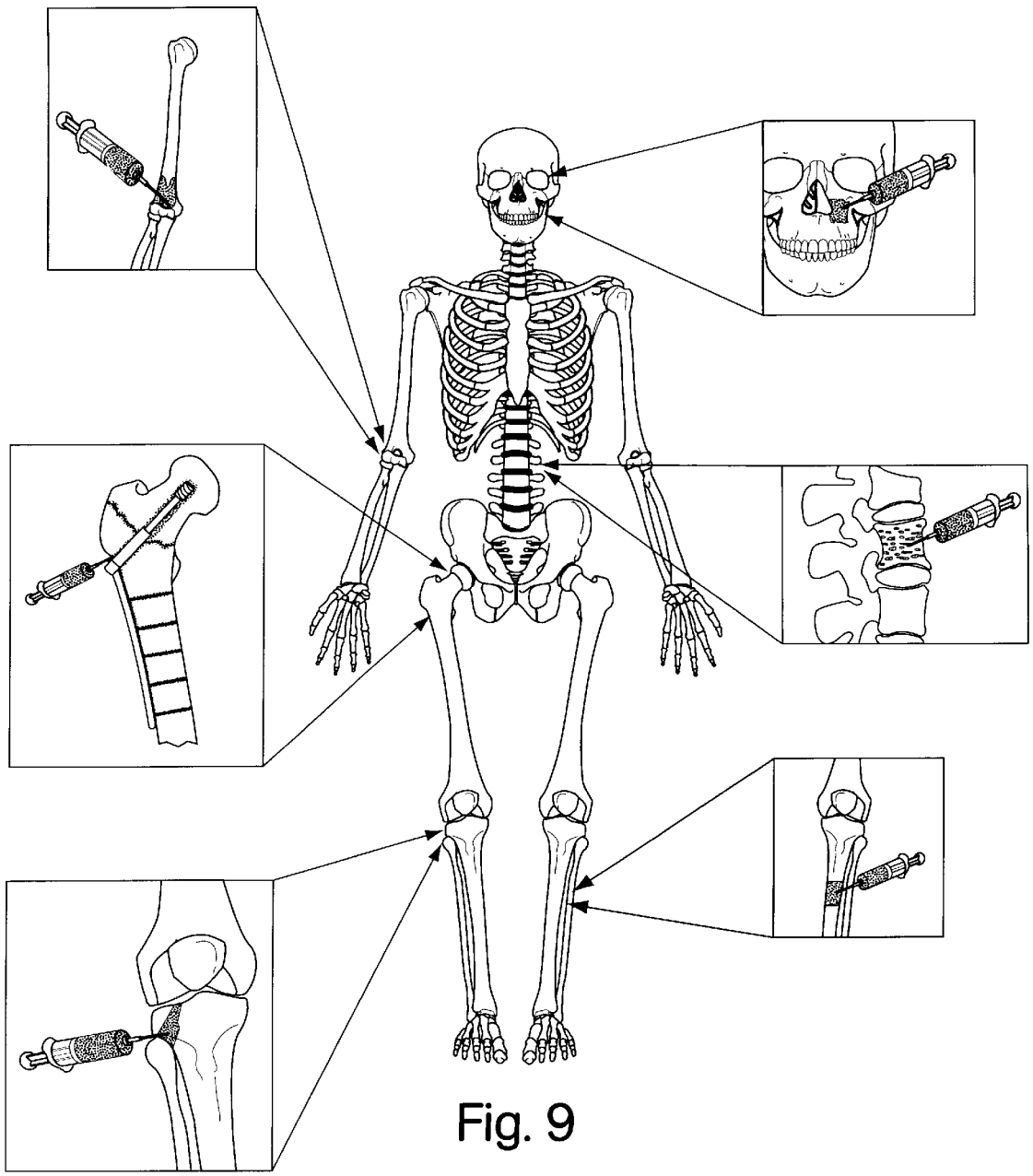
FIG. 9 depicts use of the delivery vehicle of the present invention in a variety of bony sites.
Figure 10A:
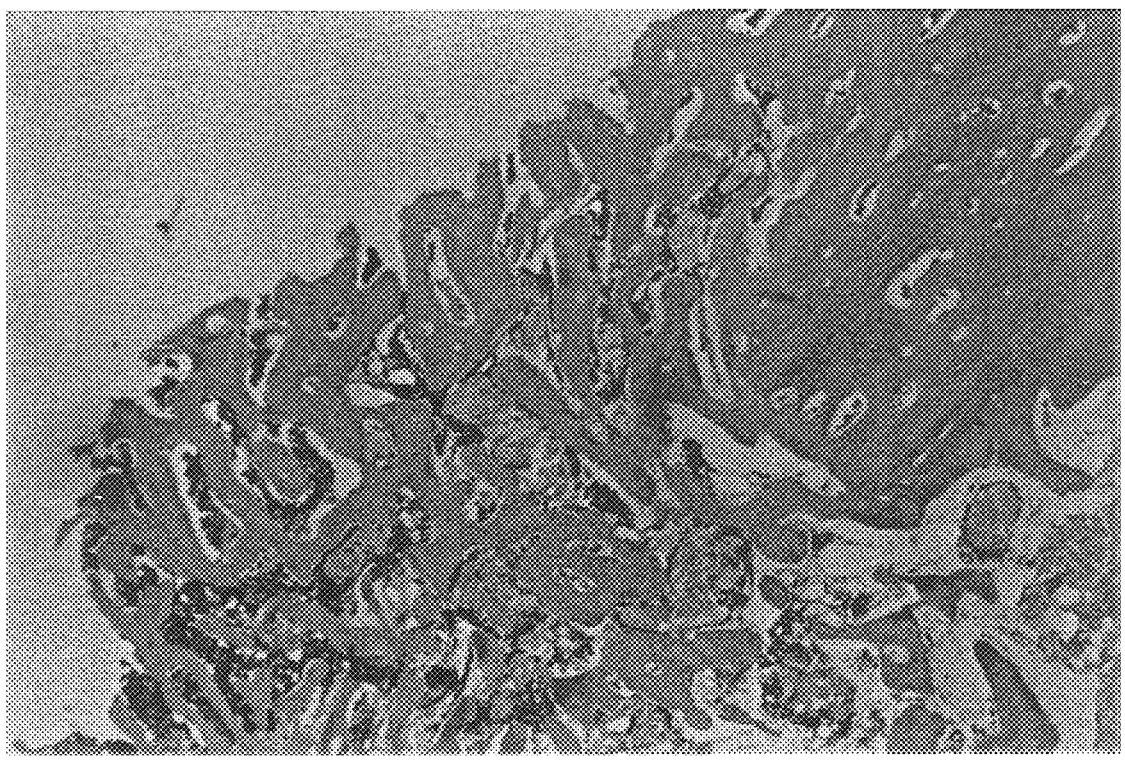
In FIG. 10a, the small arrows indicate one edge of the defect; the large arrowhead is at the yet unbridged defect.
Figure 10B:
In FIG. 10b, large arrowheads denote one edge of the defect. In both Figures, magnification is 4×, bone is decalcified, and slides are treated with hematoxylin and eosin.

Histological results indicated some mineralization at 2 weeks. By 4–6 weeks, animals receiving implants had normal trabecular bone at the implant site with no evidence of remaining PCA calcium phosphate. The untreated controls had not fully healed in that they had less than full ingrowth and/or had non-cortical-type bone. FIGS. 10a and 10b are photomicrographs of untreated and treated tibia defects, respectively, 2 weeks after surgery. As can be seen, bone to the right of the defect edge in the untreated sample (FIG. 9a) is thin trabecular bone; new bone to the right of the defect edge in the treated sample is thick trabecular bone.

Example 15

Implantation and Resorption of Drug Delivery Vehicle in a Subcutaneous Site

This example demonstrates the resorption of the inventive PCA calcium phosphate when implanted subcutaneously into rats. It also demonstrates a useful screening procedure to test resorption characteristics of new formulations of bioceramic implant materials and composites.

Eighty male and eighty female Sprague-Dawley rats were each implanted with 4 ml (2–4 gm) of the inventive PCA (prepared according to Example 4) into the dorsal subcutis (>10× the amount considered maximal in humans on a per kg basis). Control animals were treated with an equal volume of saline. Operation procedures are described in Example 16. The rats were sacrificed according to the schedule presented below in Table 3; the implant site was examined as described in Example 16.

TABLE 3

Sacrifice Schedule

| Sacrifice Timepoint | PCA calcium phosphate implant |
|---|---|
| 1 week | 5 m/5 f |
| 2 weeks | 5 m/5 f |
| 1 month | 5 m/5 f |
| 3 months | 5 m/5 fl year |
| 20 m/20 f | |

Blood for clinical pathology analyses was collected via retroorbital sinus or cardiac puncture (all by the same method) while the animals were under $CO_2$ anesthesia. Blood samples were collected from each group of animals prior to scheduled sacrifice. Clinical observations of the animals for general health and well-being were performed at least weekly until 3 months, and then monthly.

At 1 week PCA material was present at the implant site and was found associated with moderate to marked granulomas presumable associated with the resorption process. At week two a small amount of PCA material was still present at the implant site and associated granulomas were mild to moderate. By week four most tissue appeared normal with a few mild granulomas persisting at the implant site. At week twelve no evidence of the implant remained.

Example 16

Implantation and Resorption of Drug Delivery Vehicle in an Intramuscular Site.

This example describes the preparation of delivery vehicles that have varied in vivo resorption times as a result of varied grinding times. Individual dry precursors, ACP and DCPD were prepared as described in Example 4. Several different formulations of DCPD and ACP were then prepared by i) grinding DCPD for 15 sec, 30 sec, 1 min, 2.5 min, or 5 min in a SPEX grinder; ii) combining the ground DCPD 1:1 with ACP; and iii) grinding the mixture for an additional 15 sec, 30 sec, 1 min, 2.5 min, or 5 min, respectively. Total grinding times for the different preparations were therefore 30 sec, 1 min, 2 min, 5 min, and 10 min.

The PCA calcium phosphate, sterilized in powder form by approximately 2.5 Mrad of gamma irradiation, was prepared as described in Example 4 by taking the material in powder form and mixing with sterile water or saline and forming it into approximately 1 cm disks 2 mm thick and incubated for a minimum of 30 minutes at 37° C. Disks were implanted into adult male New Zealand White Rabbits immediately following fabrication.

Animals were assigned to dose groups which contained 3 males for a total of 15 animals. The implants were assigned to the rabbits randomly. 10–15 minutes prior to the surgery, the animal was premedicated with xylazine (10 mg/kg, i.m.).

The animal was then given ketamine (50 mg/kg, i.m.). The dorsal surface of the animal was clipped free of hair and washed with a betadine surgical solution and alcohol. Before the surgery the animal was monitored to be sure that is was properly anesthetized. To do this, pressure was applied to the foot pad. When there was no response, the animal was properly anesthetized. Throughout the procedure, the animal was monitored for whisker twitching and the toe-pinch reflect, which indicated that the animal was not waking up.

Using aseptic technique and a scalpel blade, an incision 1–2 cm in length was made in the skin over the m. longissimus lumborum (which lies along both sides of the spine). When the incision was made, the underlying fascia and muscle was also cut to allow the sample to pas into the muscle. The sample disk was placed directly into the muscle, being sure that the entire implant was embedded in the muscle. The muscle was closed with a single absorbable suture and the skin was stitched closed subcutaneously. Metal skin staples were used to close the external skin surface incision. Five samples were placed on each side in this manner. Each sample was placed at the end of the incision and they were approximately 1 cm apart from each other (see diagram). The samples were in the form of 7 mm by 2 mm disks weighing approximately 150 mg. The animals were monitored and were given buprenorphine (0.02–0.05 mg/jg, s.q) upon awakening. The analgesic was administered 2 times per day for three days after surgery.

The animals were radiographed immediately after the surgery and for every two weeks thereafter. The radiographs were compared to track the resorption of the materials. A standardized method was used for the radiographs to minimize any variation between timepoints.

After euthanasia, implant sites were first evaluated by gross examination. In those sites with visible implants, the implants appeared as grey to yellow solid discs. In those sites where the implant had been resorbed, areas of red to tan discoloration of the muscle were observed.

Muscle tissue, with the implants, was removed, being careful not to disturb the implants. The tissues and the identifying marks were placed into labeled jars filled with 10% neutral buffered formalin. All implant sites were processed and evaluated microscopically. Observations were made regarding the degree of focal fibrosis, focal granulomatous inflammation, and appearance of the implant (in some cases). Fibrosis was primarily seen as fibrocytes and collagen. Animals with gross resorption had fibrosis and minimal to moderate granulomatous focal inflammation. Granulomatous inflammation was seen as focal aggregates of macrophages and giant cells, often with intracytoplasmic crystals, and occasional heterophils and lymphocytes. Inflammation around the non-resorbed implants was primarily minimal to mild fibrosis and/or granulomatous inflammation, both of which are within the acceptable range for intramuscular implants.

At four weeks, the pellets made from PCA calcium phosphate implants that had been prepared by grinding for 30 seconds, 1 minute, or 2 minutes were fully resorbed. Those that had been prepared by grinding for 5 minutes or 10 minutes were not fully resorbed.

Example 17

Implantation and Resorption of Drug Delivery Vehicle in a Bony Site

The purpose of this study was to assay resorption and ossification of the PCA calcium phosphate of the invention in a bony site.

Mature (>1 year) beagle dogs were employed for this study because of their size and historical use as a model for bone studies. The tibia of the dog is large enough to allow large (>5 mm) defects to be created and studied without compressing the ability of the animal to ambulate without inducing fractures secondary to induction of defects in the bones.

Ten adult male and female beagle dogs (6.0–15.0 kg) received the same treatment; Defects were created in the lateral surface of the tibial crest cortex (8 mm or 10 mm) in each tibiae. PCA calcium phosphate was placed in the defect in one tibia and the other tibia served as a control.

An incision was made over the proximal tibia. The soft tissue was deflected away and the bone was exposed. Using an 8 mm trephine in a low speed dental handpiece with irrigation (0.9% physiologic saline) as needed, the bony disk was dissected free and the site was prepared for implantation. The inventive calcium phosphate material (solid or paste) was placed into the defect. The soft tissues were then closed in layers. One to three samples per animal were performed using this method. The animals were allowed to heal for scheduled periods of time.

Animals were assessed by clinical observations, radiographs, and microscopy of the defect sites at 0, 2, 4, and 8 weeks. Specifically, tibia radiographs were taken every 2 weeks throughout the study. The radiographs were used to determine the duration of the study. Approximately at the end of every 2 weeks, 2 animals were sacrificed and the test sites were removed for histology. The implantation sites were prepared as undecalcified and decalcified sections.

Two dogs were used as pilot animals and did not receive and PCA material. In these pilot animals, some healing was observed radiographically at 2 weeks. By 6–8 weeks, the defect was completely healed. The size of dog defects was determined to be optimal at 1 cm. In the remaining 8 dogs, control defects healed within 6 weeks; treated defects healed in 2 to 4 weeks. The quality of the bone in the control defects was thin trabecular bone; in the treated defects, the bone was thick trabecular to cortical type bone. Thus, the treated defects healed approximately 2 weeks faster than did untreated defects, and healed with better bone thickness.

Figure 11:
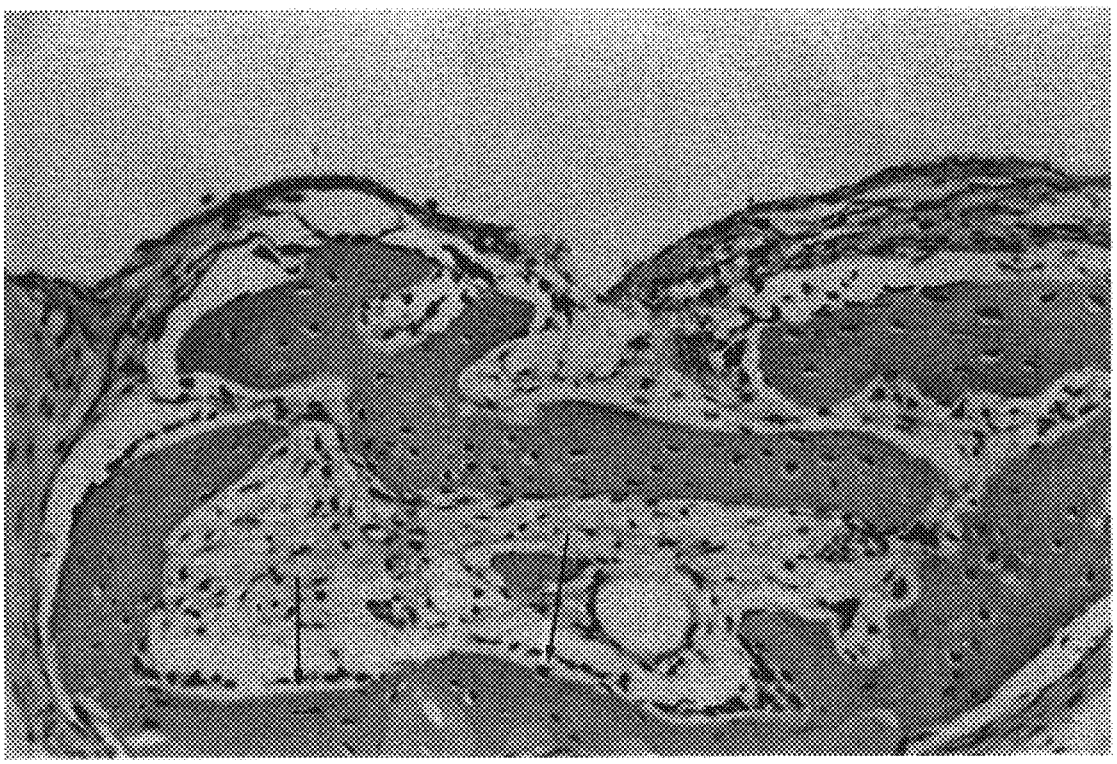
FIG. 11 is a photomicrograph of canine trabecular bone grown into a defect treated with the PCA material of the present invention. (Magnification 10×; decalcified; hematoxylin and eosin).

FIG. 11 shows a highly magnified (10×) photograph of canine trabecular bone growth into a defect site treated with the PCA material of the invention 8 weeks after surgery. The small arrows denote osteoblast—like cells lining the bone spicules and are indicative of enhanced cellular activity.

Figure 12:
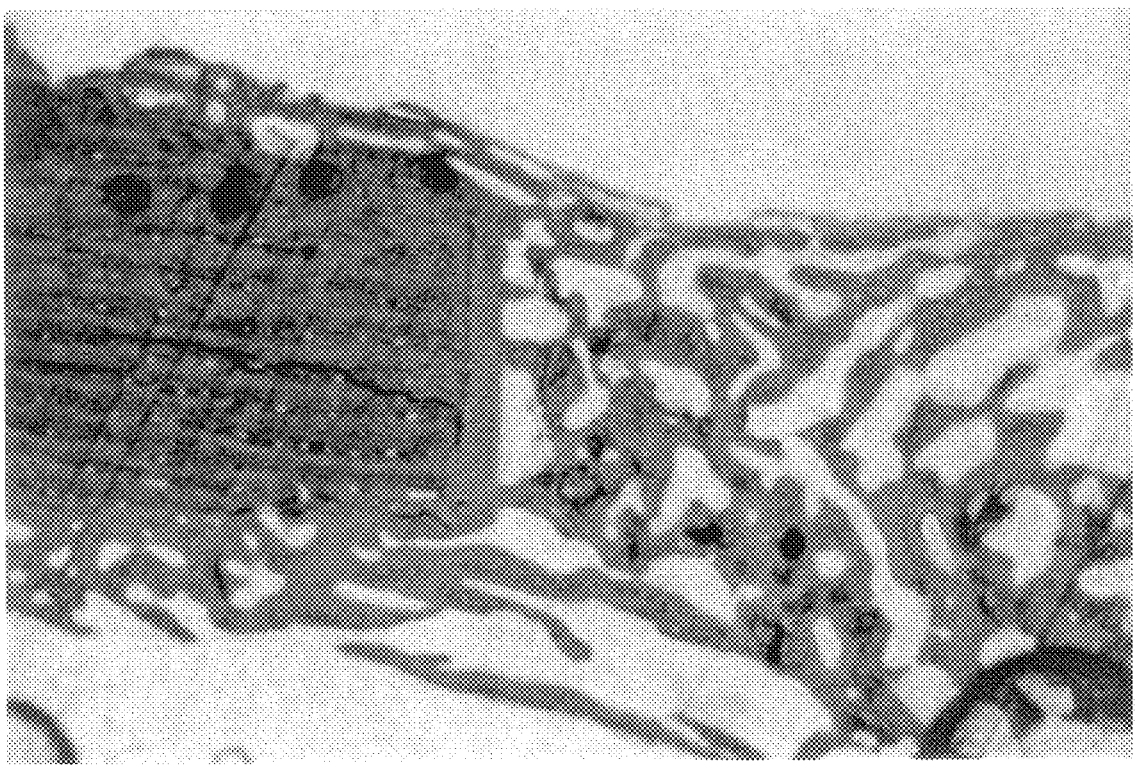
FIG. 12 is a photomicrograph of a canine cortical bone defect that was treated with the PCA material of the present invention. (Magnification 4×; undecalcified, Light Green Basic Fuchsin).

FIG. 12 shows a photomicrograph of a canine cortical bone defect treated with the PCA material of the invention. The large arrows indicate one edge of the defect. The new bone growth is to the right of the defect; at 4 weeks after surgery, this growth is thick trabecular bone.

Example 18

Implantation and Resorption of Drug Delivery Vehicle in a Bony Site

The purpose of this study was to assay resorption and ossification of the PCA calcium phosphate of the invention, and to establish parameters for screening test PCA calcium phosphate materials.

Eighteen adult (>3 month old) NZW male rabbits were used in these studies. After obtaining adequate anesthesia (e.g., ketamine/xylazine to effect), using aseptic technique, an incision was made over the proximal tibia. The soft tissue was deflected away and the bone was exposed. Using an approximately 5 mm trephine in a low speed dental handpiece with irrigation (0.9% physiologic saline) as needed, the bony disk was dissected free and the site was prepared for implantation. The inventive PCA calcium phosphate material (solid, granules or paste) was placed into the defect. The soft tissues were then closed in layers.

Clinical observations of the animals general health and well-being, with special regard to ambulation, were performed weekly and in more detail at the time of the bi-weekly radiographs. Radiographs of the tibiae were made at scheduled intervals including after surgery and at the time of necropsy.

The implantation sites were prepared as hematoxylin & eosin, Masson's trichrome decalcified samples and as undecalcified slides.

Findings and clinical observations were associated with surgery and were not associated with the PCA calcium phosphate implants. Postsurgical clinical observations were within the range of anticipated findings for surgery-related trauma. Radiographs were taken immediately postsurgery and at each scheduled sacrifice timepoint.

Immediately after surgery, all bone defect sites were distinct; implants appeared to have the same radiodensity as bone. At 2 weeks postsurgery, control defects had distinct sites and implant sites were less distinct and blended into surrounding bone; similar findings were observed at 4 weeks. At 7 weeks, all sites appeared similar with increased radiodensity. Grossly, defect sites at 2 weeks were visible clearly in control and treated animals. At 4 weeks and greater, the implant or control sites could not be grossly ascertained.

Radiographic findings indicated little change in the control animals until week 7; animals treated with inventive PCA material had increasing radiodensity in the defect over time. Defects in control animals had some new bone ingrowth, predominantly of the thin trabecular type, within 4–7 weeks. Defects in treated animals had bone ingrowth as early as 2 weeks and by 7 weeks were filled with new bone. Microscopic findings are consistent with enhanced bone replacement with PCA calcium phosphate implants. Taken together, this study shows that 5 mm defects in rabbit tibia heal or have new bone growth in control animals by 7 weeks and in animals treated with the inventive PCA material by 4 weeks. Also, this rabbit unicortical 5 mm critical sized defect model is useful to analyze test articles for there resorptive and ossificative properties.

Figure 13A:
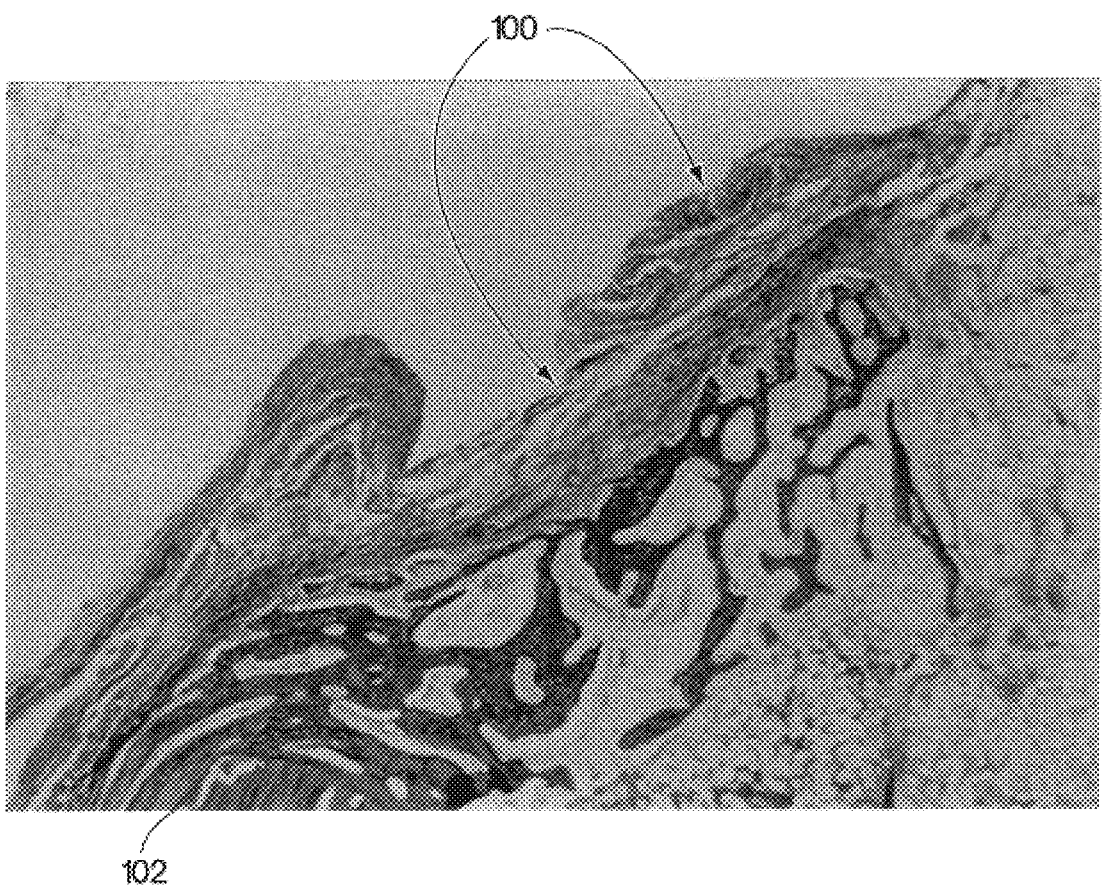
FIG. 13 presents photomicrographs of untreated (FIG. 13a) and treated (FIG. 13b) rabbit tibia defects 4 weeks after surgery (Magnification 4×; decalcified; Masson's Trichrome).
Figure 13B:
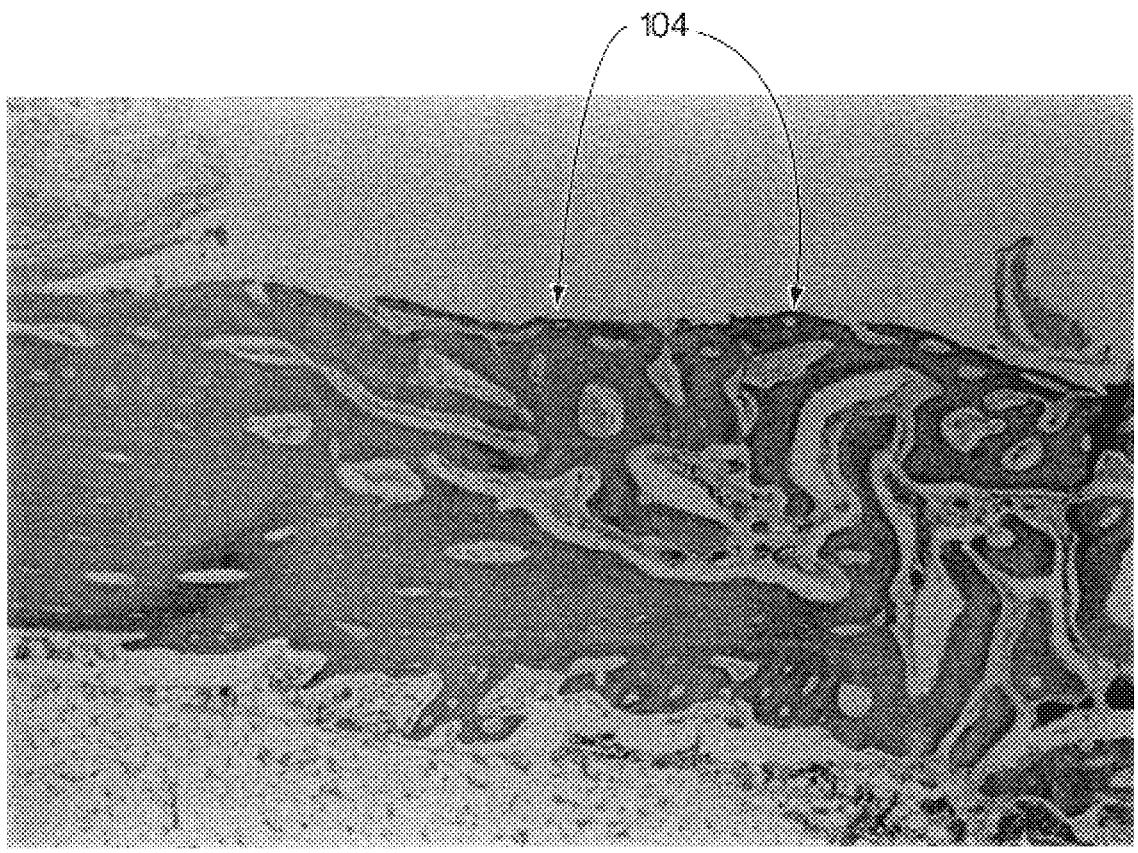
Figure 14:
FIG. 14 is a photomicrograph of a region external to a bone site in which cartilage formation has occurred (hematoxylin and eosin).

FIG. 13 shows photomicrographs of untreated (FIG. 13a) and treated (13b) rabbit tibia defects 4 weeks after surgery. The large arrow indicates the edge of the defect. In FIG. 13a, small arrows 100 denote an abundance of fibrous connective tissue on the defect site. The large arrowhead 102 points to new trabecular bone in the defect. In FIG. 13b, the two small arrows 104 demarcate the thick trabecular bone growth in the defect site.

Example 19

Variation of Resorption Rates of Synthetic PCA Materials by Varying Particle Size PCA precursor material is prepared according to Example 5. Two precursor mixes are prepared, sample A corresponding to sample 6 and sample B to a 2:4:3:1 mix of samples 1,2,3, and 4. Hydrated precursor pastes of the two samples are tested in rodents in the subcutaneous test of Example 15. Resorption is monitored at various time points.

Example 20

Pre-hardened Implant: Augmentation and Resorption in the Canine Mandibular Onlay Model The purpose of this study was to evaluate resorption, ossification and biocompatibility of two formulations of the inventive PCA calcium phosphate in canine mandibular sites. Prehardened PCA calcium phosphate was implanted in a canine mandibular onlay model which additionally may be used as an augmentation model.

The test article was PCA calcium phosphate in two formulations, corresponding to Types 2 and 10 described in Example 16. The PCA calcium phosphate was pre-hardened in a moist environment at approx. 40° C. immediately prior to implantation. The control implants were 3 mm×4 mm cylinders of silicone and porous hydroxyapatite, respectively.

Two adult female hound-type dogs (20 to 25 kg) were used in the study. Both dogs received two control implants (1 of each) on the right side of the mandible and one each of the Type 2 and Type 10 PCA calcium phosphate formulations on the left (opposite) side.

Implantation was performed under full anesthesia and aseptic surgical conditions. The animals were premedicated with tranquilizers and atropine-type agents and induced with barbiturates. The animal's vital signs (temperature, heart rate, respiratory rate) were monitored before and throughout the procedure. The animals were tested for proper anesthetic depth by toe pinch and corneal stimulus. After obtaining adequate anesthesia, using aseptic technique, an incision was made in the skin over the midlateral ventral surface of the mandible and proximal neck (over the mandible lower edge). The soft tissue was deflected away and the bone was exposed. The periosteum over the outer mandibular surface was elevated and the bone surface was roughened with a burr or drill until it was rough and bloody in a shape to accept the cylindrical implants. The control articles and pre-hardened PCA calcium phosphate were placed into the defects. Two samples per animal per side were onlaid onto each outer mandible surface using this method (two experimental PCA calcium phosphate samples and two controls). The samples were placed about 1 cm to insure that they do not appose each other. The periosteum was closed first using 3.0 vicryl. The soft tissues were then closed in layers with 3-0 vicryl absorbable suture. The skin was closed with simple interrupted sutures of 5-0 nylon. The animals were allowed to heal for scheduled periods of time. One dog was sacrificed at 3 weeks and the other at 3 months and the test sites were removed for histology. All animals were euthanized and identifying marks were collected.

The implantation sites were prepared as undecalcified sections. Sections were evaluated for biointegration, biodegradation, and biocompatibility.

The results were as follows: At all time points excellent biocompatibility was observed. No giant cells and minimal macrophage were observed. There was only minimal reaction layer of only a few cells thickness at the base of the PCA calcium phosphate implants. This is significantly better than was observed for either of the controls.

At three weeks, the majority of the Type 2 material was resorbed. At twelve weeks, the Type 2 was completely resorbed to the surface of the original bone. Additionally the bone in the socket was not fully differentiated.

The Type 10 samples demonstrated osseointegration with new bone ingrowth and cell migration into the implant. The implant itself was approximately 10% resorbed after twelve weeks.

The silicon control implant, which is not resorbable, displayed a mild to moderate foreign body reaction. Voids were unfilled at three weeks, but by twelve weeks were filled with fibrous tissue. The hydroxyapatite control implant showed no signs of resorption or osseointegration within the first twelve weeks.

This experiment confirms the excellent biocompatibility of the inventive PCA calcium phosphate. Additionally, a difference in resorption time between the two PCA formulations was observed, with a prolonged resorption time course for the sample in which the precursors were mixed/ground for a longer period of time (Type B).

The results also point out the slower resorption and ossification properties observed in the non-load bearing mandible implant site as compared to rapidly ossifying load bearing applications of Examples 14, 17 and 18.

Example 21

Ectopic Bone Production

This example describes the production of ectopic bone in an animal model using an inventive cell seeded PCA material.

The PCA material is prepared and implanted either subcutaneously or imtramuscularly as described examples 15 and 16, except that the material is not pre-hardened, the hydration medium used is 0.8 ml/gm phosphate buffered saline pH 7.4, and the material is seeded with cells as described below. In some instances 0.2 mg/ml of BMP 7 is included in the hydration medium.

Prior to implantation, the 1 g sample of hydrated PCA is inoculated using a syringe with approximately 50 $\mu$l of the subject's bone marrow harvested previously with a biopsy needle. The hydrated precursor is then implanted. Enough subjects are used to allow recovery of the PCA on a biweekly basis to study ectopic bone production.

Example 22

Production of Cartilage in vivo with Autologous Cell Seeding

This example describes the production of cartilage on the surface of a bone from an inventive PCA material composition seeded with autologous cartilage-producing cells.

In a number of instances involving dogs and rabbits, unexpected formation of cartilage was observed when bone that had been treated with PCA material was histologically examined. FIG. 18 is a photomicrograph of a radial bone from a NZW rabbit, stained with hematoxylin and eosin. A small mound of PCA material had been inadvertently applied to a region of healthy bone, and the formation of cartilage is clearly observed in the center of the mound of PCA. Native bone is designated as 2 and cartilagenous region is indicated at 1.

Example 23

Production of Cartilage in vitro

This example describes the in vitro production of cartilage from a cell-seeded PCA material composition of the present invention.

Human chondrocytes are prepared and cartilage production determined according to Goldring (*Methods in Molecular Medicine Human Cell Culture Protocols,* Edited by Jones, Human Press, pp. 217–232, 1996, incorporated herein by reference); rat cell line CFK2 is maintained according to Bernier et al. (1993 *J. Bone Miner. Res.* 8: 475, 1993); and articular and intervertebral chondrocytes are prepared according to Rivard et .al. (Fifth World Biomaterials Congress, pg. 291, 1996). All procedures are performed aseptically under sterile conditions.

Sterile PCA hydrated precursor is prepared according to example 5, sample 5. Hydration medium is 2×HBSS (50 mM HEPES, 10 mM KCl, 280 mM NaCl and 12 mM glucose pH 7.5). The hydrated precursor is formed into two slabs, each of which is about 1 mm thick and approximately 1 cm square. A small indentation is prepared in the first slab, and about 25,000 cells in approximately 5 µl of growth medium containing 10% FCS are placed within the well. The second slab is placed on top of the first slab, and edges of the two slabs are gently pinched together. The resultant composition is placed in a petri dish so that it is submerged in growth medium containing 10% FCS. The petri dish is placed in an incubator at 37° C. in 5% $CO_2$. The medium is changed every three to four days. Enough replicates are prepared to analyze a sample on a weekly basis for the formation of cartilage.

Example 24

Ectopic Cartilage Formation

This example describes the production of ectopic cartilage in an animal model using an inventive cell-seeded PCA material composition.

The PCA material is prepared and implanted either subcutaneously or intramuscularly into rabbits as described in examples 15 and 16, except that the material is not pre-hardened, the hydration medium used is 0.8 ml/gm phosphate buffered saline pH 7.4, and the PCA material is seeded with cells as described below. In some instances, 0.2 mg/ml of type 1 collagen is included in the hydration medium.

Prior to implantation, the 1 g sample of hydrated PCA is inoculated with approximately 100 µl of enzymatically-isolated autologous knee joint cartilage chondrocytes. Preferably, the chondrocytes are delivered into the PCA material using a syringe. The cell-seeded hydrated precursor is implanted. Enough subjects are used to allow recovery of the PCA on a biweekly basis to study ectopic cartilage production.

Example 25

In vivo Cartilage Repair

This example describes the production of ectopic cartilage in an animal model using an inventive cell-seeded PCA material composition.

A PCA material hydrated precursor is prepared and implanted into dog knee joints in which cartilage has been surgically removed. The hydration medium used is 0.8 ml/gm phosphate buffered saline pH 7.4, and the hydrated precursor is seeded with cells as described below. In some instances 0.2 mg/ml of type 1 collagen is included in the hydration medium.

Prior to implantation, the 1 g sample of hydrated precursor material is inoculated with approximately 200 µl of enzymatically isolated autologous knee joint cartilage chondrocytes. The chondrocytes are preferably delivered by syringe. The cell-seeded hydrated precursor is implanted. Enough subjects are used to allow recovery of the PCA on a biweekly basis to study joint cartilage production.

Example 26

Cell Encapsulation Matrix

This example describes the use of inventive PCA matrices for encapsulated cell therapy. Encapsulation devices are prepared according to known methods (see Aebischer et al., U.S. Pat. No. 4,892,538; Sefton et al., U.S. Pat. No. 4,353,888; Winn et al. *Experimental Neurology* 140:126 (1996), each of which is incorporated herein by reference).

Devices are loaded with hydrated precursor paste in the presence of 15,000 fibroblasts and sealed. Devices are maintained in vitro or implanted into animal recipients. Devices are explanted periodically and checked with trypan blue for cell viability.

Example 27

In vivo Augmentation with a PCA/HA Composite

This Example demonstrates the use of a relatively slowly resorbing PCA material in a PCA/HA composite to produce a long lasting, shape-retaining skeletal augmentation.

PCA/HA composites are prepared by mixing particulate HA (grain size <200 µm) with the inventive hydrated precursor putty described in example 5, sample 5, in a ratio ranging from 0.05 to 30% wt/vol. The granular putty produced by this mixing is shaped in a form suitable for implantation. The granular putty is then hardened at 37° C.

The implant site is prepared by dissecting away a few millimeters of the cortical bone, including the periosteum. If possible, the periosteum is peeled back from the cortical bone surface at the implant site, but is left attached. The material and blood from the dissected bone is retained and mixed with fresh PCA material paste (i.e., hydrated precursor) in about a 1:3 vol/vol ratio, and is set aside. Fresh PCA material paste is used as a cement to affix the implant to exposed cortical bone surface. Additional PCA material paste is applied as needed to ensure adherence of the implant. The retained PCA/tissue material mix is then used as a seeding source for the implant and is applied to as much of the implant surface as is possible. The periosteum is then drawn back over the implant as much as possible.

Other Embodiments

As will be clear to those of ordinary skill in the art, the forgoing has been merely a description of certain preferred embodiments of the invention. Various changes and modifications to the described embodiments may be made without departing from the spirit or scope of the invention, as set forth in the following claims.

What is claimed is:

1. A method for preparing a therapeutic, structural or cosmetic implant, comprising:
   a. providing a composition in hydrated precursor form, wherein the hydrated precursor is capable of conversion into a hardened poorly crystalline apatitic (PCA) calcium phosphate;
   b. promoting conversion of the hydrated precursor so that the composition becomes hardened PCA calcium phosphate; and
   c. introducing at least one cell into the composition prior to hardening of the hydrated precursor.

2. The method of claim 1 wherein the step of providing comprises providing a hydrated precursor comprising:
   a. an amorphous calcium phosphate (ACP) precursor;
   b. a second precursor selected from the group consisting of: a calcium source, a phosphate source, combinations of calcium and phosphate sources, and calcium phosphates; and
   c. a limited amount of an aqueous solution.

3. The method of claim 2 wherein the aqueous solution is a buffered solution selected for compatibility with the at least one cell.

4. The method of claim 2 wherein the cell is selected from the group consisting of chondrocytes, osteocytes, osteoblasts, osteoclasts, mesenchymal stem cells, fibroblasts, muscle cells, hepatocytes, parenchymal cells, cells of intestinal origin, nerve cells, and skin cells.

5. The method of claim 2 wherein the at least one cell comprises at least one tissue-forming cell.

6. The method of claim 2 wherein the at least one cell comprises at least one bone-forming cell.

7. The implant of claim 2 wherein the at least one cell comprises at least one cartilage-forming cell.

8. The method of claim 2 wherein the at least one cell comprises a tissue-degrading cell.

9. The method of claim 2 wherein the step of introducing at least one cell comprises introducing a sufficient number of cells so that the PCA calcium phosphate is populated by at least about 20,000–1,000,000 cells/cm$^3$.

10. The method of claim 2, further comprising a step of shaping the hydrated precursor into a pre-determined form prior to hardening.

11. The method of claim 2, further comprising a step of shaping the hardened PCA calcium phosphate into a pre-determined form.

12. The method of claim 1 wherein the step of promoting conversion involves exposing the hydrated precursor to appropriate conditions for a time sufficient that a PCA calcium phophate characterized by an X-ray diffraction pattern comprising broad peaks at 2θ values of 26°, 28.5°, 32°, and 33° is produced.

13. The method of claim 1 wherein the step of promoting conversion involves exposing the hydrated precursor to appropriate conditions for a time sufficient that a PCA calcium phophate characterized by a calcium to phosphate ratio of less than about 1.5 is produced.

14. The method of claim 1 wherein the step of promoting conversion involves exposing the hydrated precursor to appropriate conditions for a time sufficient to produce a PCA calcium phophate characterized in that, when a vehicle comprising at least 1 g of PCA calcium phosphate is formed, at least about 80% of the PCA calcium phosphate is resorbed within one year when the vehicle is placed in a rat intramuscular site.

15. The method of claim 1 wherein the step of promoting conversion involves exposing the hydrated precursor to appropriate conditions for a time sufficient to produce a PCA calcium phophate characterized in that, when a vehicle comprising at least 1 g of PCA calcium phosphate is formed, at least about 80% of the PCA calcium phosphate is resorbed within 9 months when the vehicle is placed in a rat intramuscular site.

16. The method of claim 1 wherein the step of promoting conversion involves exposing the hydrated precursor to appropriate conditions for a time sufficient to produce a PCA calcium phophate characterized in that, when a vehicle comprising at least 1 g of PCA calcium phosphate is formed, at least about 80% of the PCA calcium phosphate is resorbed within 6 months when the vehicle is placed in a rat intramuscular site.

17. The method of claim 1 wherein the step of promoting conversion involves exposing the hydrated precursor to appropriate conditions for a time sufficient to produce a PCA calcium phophate characterized in that, when a vehicle comprising at least 1 g of PCA calcium phosphate is formed, at least about 80% of the PCA calcium phosphate is resorbed within 3 months when the vehicle is placed in a rat intramuscular site.

18. The method of claim 1 wherein the step of promoting conversion involves exposing the hydrated precursor to appropriate conditions for a time sufficient to produce a PCA calcium phophate characterized in that, when a vehicle comprising at least 1 g of PCA calcium phosphate is formed, at least about 80% of the PCA calcium phosphate is resorbed within 1 month when the vehicle is placed in a rat intramuscular site.

19. The method of claim 1 wherein the step of promoting conversion involves exposing the hydrated precursor to appropriate conditions for a time sufficient to produce a PCA calcium phophate characterized in that it is fully resorbable.

20. The method of claim 2 wherein the step of providing comprises providing a hydrated precursor that is a paste.

21. The method of claim 20 wherein the step of promoting comprises allowing the hydrated precursor to harden at 22° C. for a time longer than one hour.

22. The method of claim 20 wherein the step of promoting comprises allowing the hydrated precursor to harden at 37° C. for a time shorter than one hour.

23. The method of claim 22 wherein the step of promoting comprises allowing the hydrated precursor to harden at 37° C. for about 10–30 minutes.

24. The method of claim 1 or claim 2 further comprising, prior to the step of promoting, a step of combining with the hydrated precursor an addtional material selected to change a physical parameter of the vehicle, which physical parameter is selected from the group consisting of: strength, resorption time, adherence, injectability, frictional characteristics, and release kinetics.

25. The method of claim 2 further comprising, prior to the step of promoting, a step of combining with the hydrated precursor a biologically active agent.

26. The method of claim 2 wherein the biologically active agent is one that affects a process selected from the group consisting of cell growth, cell migration, cell differentiation, and cell localization.

27. The method of claim 26 wherein the biologically active agent is selected from the group consisting of growth factors and extracellular matrix components.

28. The method of claim 26 werein the biologically active agent is selected from the group consisting of lamin, fibronectin, collagen, and combinations thereof.

29. The method of claim 26 wherein the biologically active agent is selected from the group consisting of nutrients, angiogenic factors, and immunomodulatory factors.

30. A method for preparing a structural implant comprising:
  a. providing a composition in hydrated precursor form, wherein the hydrated precursor is capable of conversion into a hardened poorly crystalline apatitic (PCA) calcium phosphate;
  b. promoting conversion of the hydrated precursor so that the composition becomes hardened PCA calcium phosphate, said PCA calcium phosphate composition having sufficient tensile strength, hardness and fracture toughness so that said PCA calcium phosphate composition is capable of serving as a structural implant in a living organism; and
  c. before or after step b, introducing at least one cell into the composition.

* * * * *

UNITED STATES PATENT AND TRADEMARK OFFICE
CERTIFICATE OF CORRECTION

PATENT NO. : 6,139,578
APPLICATION NO. : 09/023344
DATED : October 31, 2000
INVENTOR(S) : Lee et al.

It is certified that error appears in the above-identified patent and that said Letters Patent is hereby corrected as shown below:

On Title Page Item (56)
Page 1, References Cited, Foreign Patent Documents, replace "0 268 463 2/1998" with
--0 268 463 5/1998--.

On Title Page Item (56)
Page 2, References Cited, Other Publications, replace "Barton et al" with
--Barton et al.--.

On Title Page Item (56)
Page 2, References Cited, Other Publications, replace "Ducheyne et al., "Bioceramic Composites", Chapter 15 from "An Introduction to Bioceramics, Advanced Series in Ceramics", vol. I." with
--Ducheyne et al., "Bioceramic Composites", Chapter 15 from "An Introduction to Bioceramics, Advanced Series in Ceramics", Vol. I.--.

On Title Page Item (56)
Page 2, References Cited, Other Publications, replace "Etex (Knaack et al) "Novel Fully Resorbable Calcium Phosphate Bone Substitute" 1997 *ASBMR Abstract*, vol. 12, Supplement 1 :s202 Aug., 1997." with --Etex (Knaack et al.) "Novel Fully Resorbable Calcium Phosphate Bone Substitute" 1997 *ASBMR Abstract*, Vol. 12, Supplement 1:s202 Aug., 1997.--.

On Title Page Item (56)
Page 3, References Cited, Other Publications, replace "Ishaug et al., "Osteoblast function on synthetic biodegradable polymers" *J. Biomed.Mater.Res.* 28:1445, Dec. 1994." With --Ishaug et al., "Osteoblast Function on Synthetic Biodegradable Polymers," *J. Biomed. Mater. Res.* 28: 1445, Dec. 1994.--.

On Title Page Item (56)
Page 3, References Cited, Other Publications, replace "Suzuki et al., "Identification Macrophage Migration Inhibitoty Gactor in Murine Neonatal Clavariae and Osteoblasts", $43^{rd}$ *Ann. Mtng, Orthop. Res. Soc.*, Feb. 9-13, 1997, San Francisco, CA." with --Suzuki et al., "Identification Macrophage Migration Inhibitory Factor in Murine Neonatal Clavariae and Osteoblasts", $43^{rd}$ *Ann. Mtng, Orthop. Res. Soc.*, Feb. 9-13, 1997, San Francisco, CA.--.

Column 8, Line 7, replace "that it useful in the" with --that is useful in the--.

Column 10, Line 49, replace "(including cancerous bone)" with --(including cancellous bone)--.

UNITED STATES PATENT AND TRADEMARK OFFICE
CERTIFICATE OF CORRECTION

PATENT NO. : 6,139,578
APPLICATION NO. : 09/023344
DATED : October 31, 2000
INVENTOR(S) : Lee et al.

It is certified that error appears in the above-identified patent and that said Letters Patent is hereby corrected as shown below:

Column 12, Line 38, replace "or other method of factor" with --or other methods of factor--.

Column 13, Line 67, replace "contains peaks characteristic" with --contains peak characteristics--.

Column 14, Line 25, replace "separating each granules" with --separating each granule--.

Column 15, Line 23, replace "by heating 37°C" with --by heating at 37°C--.

Column 16, Line 17, replace "Examples" with --Example--.

Column 17, Insert new line after line 62, centered text "Example 14"

Column 19, Line 34, replace "presumable associated" with --presumably associated--.

Column 20, Line 14, replace "to pas into" with --to pass into--.

Column 21, Lines 32-33, replace "did not receive and PCA material" with --did not receive any PCA material--.

Column 22, Lines 42-43: Replace "test articles for there resorptive" with --test articles for their resorptive--.

Column 24, Line 65, replace "Rivard et .al." with --Rivard et al.--.

Column 26, Line 66, replace "with the at" with --with at--.

Column 27, Line 8, replace "The mathod" with --The method--.

Column 27, Line 10, replace "The implant" with --The method--.

Column 27, Line 27, replace "calcium phophate" with --calcium phosphate--.

Column 27, Line 33, replace "calcium phophate" with --calcium phosphate--.

Column 27, Line 38, replace "calcium phophate" with --calcium phosphate--.

Column 27, Line 46, replace "calcium phophate" with --calcium phosphate--.

Column 27, Line 54, replace "calcium phophate" with --calcium phosphate--.

UNITED STATES PATENT AND TRADEMARK OFFICE
CERTIFICATE OF CORRECTION

PATENT NO. : 6,139,578
APPLICATION NO. : 09/023344
DATED : October 31, 2000
INVENTOR(S) : Lee et al.

It is certified that error appears in the above-identified patent and that said Letters Patent is hereby corrected as shown below:

Column 27, Line 62, replace "calcium phophate" with --calcium phosphate--.

Column 28, Line 4, replace "calcium phophate" with --calcium phosphate--.

Column 28, Line 12, replace "calcium phophate" with --calcium phosphate--.

Column 28, Line 27, replace "addtional" with --additional--.

Column 28, Line 35, replace "claim 2" with --claim 25--.

Column 28, Line 43, replace "werein" with --wherein--.

Signed and Sealed this

Twentieth Day of February, 2007

JON W. DUDAS
*Director of the United States Patent and Trademark Office*